(12) United States Patent
Abdou

(10) Patent No.: US 7,618,443 B2
(45) Date of Patent: Nov. 17, 2009

(54) OCCIPITO FIXATION SYSTEM AND METHOD OF USE

(76) Inventor: M. Samy Abdou, 7790 Doug Hill, San Diego, CA (US) 92127

( * ) Notice: Subject to any disclaimer, the term of this patent is extended or adjusted under 35 U.S.C. 154(b) by 451 days.

(21) Appl. No.: 11/153,258

(22) Filed: Jun. 14, 2005

(65) Prior Publication Data

US 2005/0288669 A1    Dec. 29, 2005

Related U.S. Application Data

(60) Provisional application No. 60/579,531, filed on Jun. 14, 2004, provisional application No. 60/659,675, filed on Mar. 7, 2005.

(51) Int. Cl.
*A61B 17/88* (2006.01)
(52) U.S. Cl. .................. 606/278; 606/281; 606/286; 606/267; 606/280
(58) Field of Classification Search .............. 606/246, 606/280, 286, 260, 270, 274, 267, 268, 269, 606/271, 272, 70, 71, 281, 282, 283, 284, 606/285, 287, 288, 289, 290, 291, 292, 293, 606/294, 295, 297, 298, 299, 250, 251, 252, 606/253, 254, 255, 256, 257, 258, 259, 261, 606/262, 263, 264, 265, 266, 273, 275, 276, 606/277, 278, 279
See application file for complete search history.

(56) References Cited

U.S. PATENT DOCUMENTS 2,248,054 A    7/1941  Becker
3,659,595 A    5/1972  Haboush
4,289,123 A    9/1981  Dunn
4,773,402 A *  9/1988  Asher et al. ................ 606/250
4,903,692 A    2/1990  Reese (Continued)

FOREIGN PATENT DOCUMENTS

EP    1180348    2/2002

(Continued)

OTHER PUBLICATIONS

Derwent English Abstract for French Patent Publication FR 2781359, published Jan. 28, 2000, entitled: "Osteosynthesis frame for spinal surgery has rod with clamps to hold cross bars with anchor screws". Accession No. 9867555.

(Continued)

*Primary Examiner*—Eduardo C Robert
*Assistant Examiner*—Jan Christopher Merene
(74) *Attorney, Agent, or Firm*—Fred C. Hernandez; Mintz, Levin, Cohn, Ferris, Glovsky and Popeo P.C.

(57) ABSTRACT

Disclosed is a multi-axial occipito-cervical connection system that enables an occipital rod to be coupled to a cervical rod in a manner that permits multi-axial, relative movement between the two rods about a predetermined location, such as the heads of the rods. The system includes a locking mechanism that can be actuated to lock the relative positions of the rods. The rods can provide an interconnection between one or more attachments on the skull (such as an occipital attachment) and one or more attachments to the spine (such as spine screws).

13 Claims, 34 Drawing Sheets

U.S. PATENT DOCUMENTS

| | | | |
|---|---|---|---|
| 5,133,717 A | 7/1992 | Chopin | |
| 5,275,601 A | 1/1994 | Gogolewski et al. | |
| 5,354,292 A | 10/1994 | Braeuer et al. | |
| 5,360,429 A | 11/1994 | Jeanson et al. | |
| 5,364,399 A | 11/1994 | Lowery et al. | |
| 5,366,455 A * | 11/1994 | Dove et al. | 606/250 |
| 5,484,440 A | 1/1996 | Allard | |
| 5,531,747 A | 7/1996 | Ray | |
| 5,545,164 A | 8/1996 | Howland | |
| 5,549,612 A | 8/1996 | Yap et al. | |
| 5,558,674 A | 9/1996 | Heggeness et al. | |
| 5,578,034 A | 11/1996 | Estes | |
| 5,616,142 A | 4/1997 | Yuan et al. | |
| 5,672,176 A | 9/1997 | Biedermann et al. | |
| 5,676,666 A | 10/1997 | Oxland et al. | |
| 5,681,311 A | 10/1997 | Foley et al. | |
| 5,681,312 A | 10/1997 | Yuan et al. | |
| 5,713,900 A | 2/1998 | Benzel et al. | |
| 5,735,853 A | 4/1998 | Olerud | |
| 5,928,233 A | 7/1999 | Apfelbaum et al. | |
| 5,954,722 A | 9/1999 | Bono | |
| 5,971,987 A | 10/1999 | Huxel et al. | |
| 5,993,449 A | 11/1999 | Schlapfer et al. | |
| 6,039,740 A | 3/2000 | Olerud | |
| 6,059,786 A | 5/2000 | Jackson | |
| 6,117,135 A | 9/2000 | Schlapfer et al. | |
| 6,139,549 A | 10/2000 | Keller | |
| 6,152,927 A | 11/2000 | Farris et al. | |
| D440,311 S | 4/2001 | Michelson | |
| 6,224,602 B1 | 5/2001 | Hayes | |
| 6,235,034 B1 | 5/2001 | Bray | |
| D449,692 S | 10/2001 | Michelson | |
| 6,306,136 B1 | 10/2001 | Baccelli | |
| 6,309,391 B1 | 10/2001 | Crandall et al. | |
| 6,331,179 B1 | 12/2001 | Freid et al. | |
| 6,368,320 B1 * | 4/2002 | Le Couedic et al. | 606/250 |
| 6,402,752 B2 | 6/2002 | Schaffler-Wachter et al. | |
| 6,454,769 B2 | 9/2002 | Wagner et al. | |
| 6,524,315 B1 | 2/2003 | Selvitelli et al. | |
| 6,547,790 B2 | 4/2003 | Harkey, III et al. | |
| 6,599,290 B2 | 7/2003 | Bailey et al. | |
| 6,602,255 B1 | 8/2003 | Campbell et al. | |
| 6,602,256 B1 | 8/2003 | Hayes | |
| 6,626,907 B2 | 9/2003 | Campbell et al. | |
| 6,645,207 B2 | 11/2003 | Dixon et al. | |
| 6,652,525 B1 | 11/2003 | Assaker et al. | |
| 6,663,631 B2 | 12/2003 | Kuntz | |
| 6,663,632 B1 | 12/2003 | Frigg | |
| 6,666,867 B2 | 12/2003 | Ralph et al. | |
| 6,695,846 B2 | 2/2004 | Richelsoph et al. | |
| 6,830,571 B2 | 12/2004 | Lenke et al. | |
| 6,855,147 B2 | 2/2005 | Harrington | |
| 6,885,243 B2 | 4/2005 | Berstein et al. | |
| 7,232,441 B2 * | 6/2007 | Altarac et al. | 606/250 |
| 7,303,563 B2 * | 12/2007 | Poyner et al. | 606/279 |
| 2001/0047172 A1 | 11/2001 | Foley et al. | |
| 2002/0016595 A1 | 2/2002 | Michelson | |
| 2002/0055741 A1 | 5/2002 | Schlaper et al. | |
| 2002/0099386 A1 | 7/2002 | Beger et al. | |
| 2002/0143328 A1 | 10/2002 | Schluzas et al. | |
| 2002/0183755 A1 | 12/2002 | Michelson et al. | |
| 2002/0188296 A1 | 12/2002 | Michelson | |
| 2003/0078583 A1 | 4/2003 | Biedermann et al. | |
| 2003/0125741 A1 * | 7/2003 | Biedermann et al. | 606/61 |
| 2003/0153913 A1 | 8/2003 | Altarac et al. | |
| 2004/0133207 A1 | 7/2004 | Abdou | |
| 2004/0153070 A1 | 8/2004 | Barker et al. | |
| 2004/0204712 A1 | 10/2004 | Kolb et al. | |
| 2004/0204713 A1 | 10/2004 | Abdou | |
| 2005/0004573 A1 | 1/2005 | Abdou | |
| 2005/0010227 A1 | 1/2005 | Paul | |
| 2005/0177163 A1 | 8/2005 | Abdou | |
| 2005/0228376 A1 * | 10/2005 | Boomer et al. | 606/61 |
| 2005/0273120 A1 | 12/2005 | Abdou | |
| 2005/0283153 A1 | 12/2005 | Poyner et al. | |
| 2006/0074488 A1 | 4/2006 | Abdou | |
| 2006/0149278 A1 | 7/2006 | Abdou | |
| 2006/0155284 A1 * | 7/2006 | Doherty et al. | 606/69 |
| 2006/0161154 A1 * | 7/2006 | McAfee | 606/61 |
| 2006/0195089 A1 * | 8/2006 | LeHuec et al. | 606/61 |
| 2006/0217710 A1 | 9/2006 | Abdou | |
| 2006/0229615 A1 | 10/2006 | Abdou | |
| 2007/0093828 A1 | 4/2007 | Abdou | |
| 2007/0106383 A1 | 5/2007 | Abdou | |
| 2007/0118121 A1 * | 5/2007 | Purcell et al. | 606/61 |
| 2007/0123869 A1 * | 5/2007 | Chin et al. | 606/61 |
| 2007/0123873 A1 | 5/2007 | Abdou | |
| 2008/0051783 A1 * | 2/2008 | Null et al. | 606/61 |
| 2008/0147123 A1 * | 6/2008 | Schermerhorn | 606/278 |

FOREIGN PATENT DOCUMENTS

| | | |
|---|---|---|
| FR | 2781359 | 1/2000 |
| FR | 2856271 | 12/2004 |
| WO | 2004/032726 | 4/2004 |
| WO | 2004/062482 | 7/2004 |
| WO | 2004/093702 | 11/2004 |
| WO | WO 2005/122922 | 12/2005 |
| WO | WO 2006/041963 | 4/2006 |
| WO | WO 2006/058221 | 6/2006 |
| WO | WO 2006/089292 | 8/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |

OTHER PUBLICATIONS

Derwent English Abstract for French Patent Publication FR 2856271, published Dec. 24, 2004, Osteo-synthesis vertebral column plate, has connection head integrated with plate and movable in three directions of space so as to adapt itself to connection rod, and including opening to faciliatate introduction of rod. Accession No. 4694557.

* cited by examiner

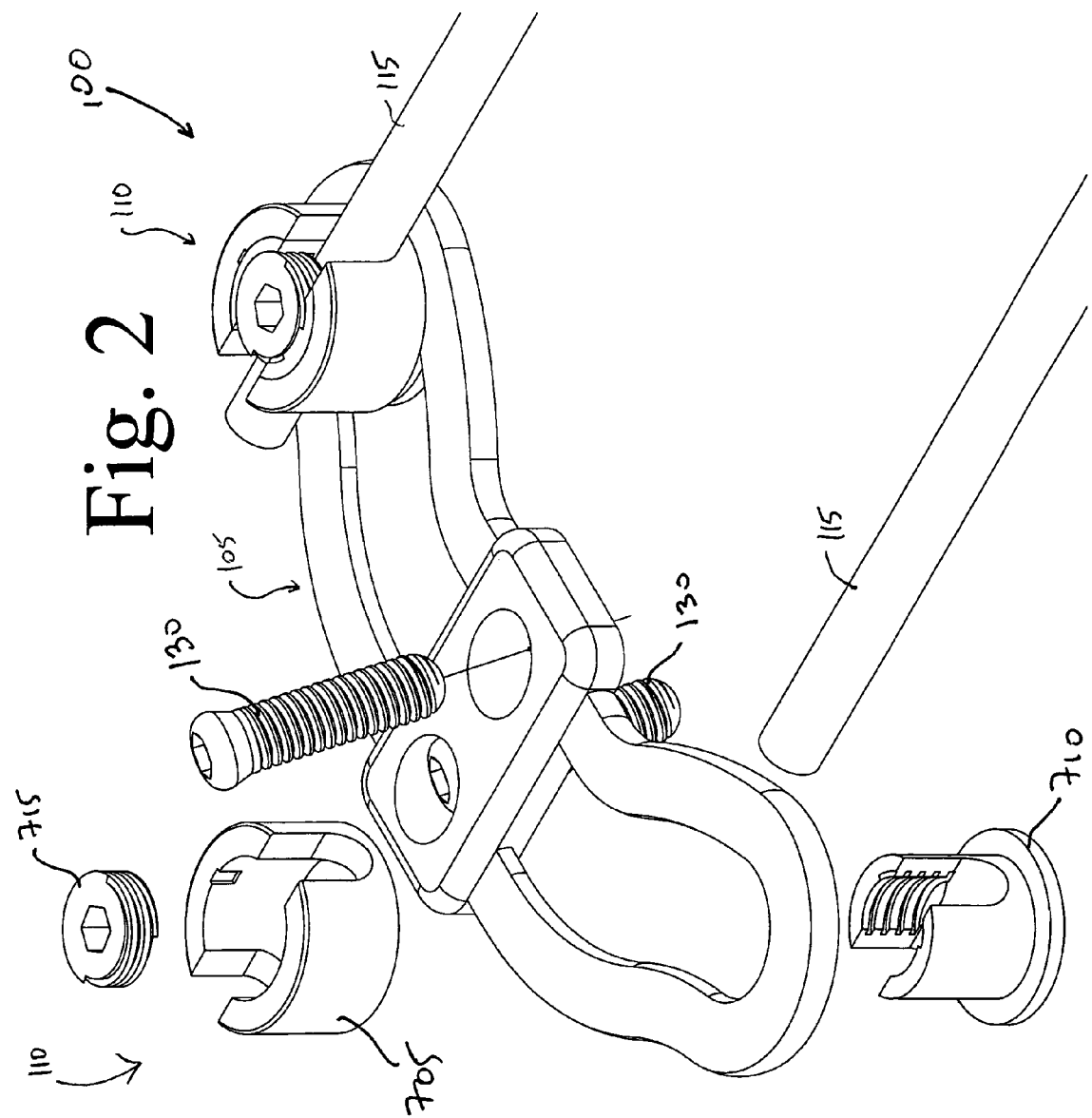

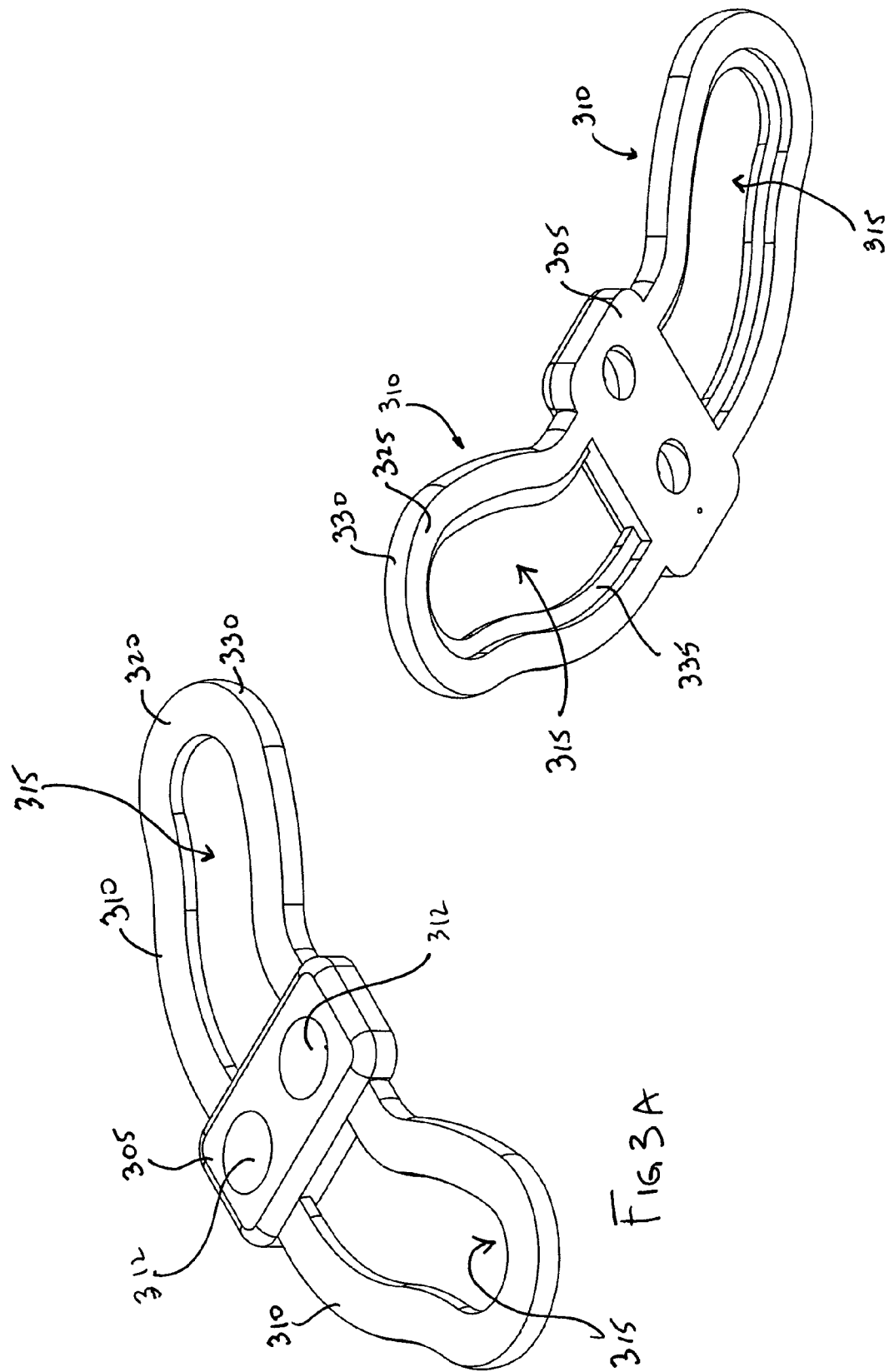

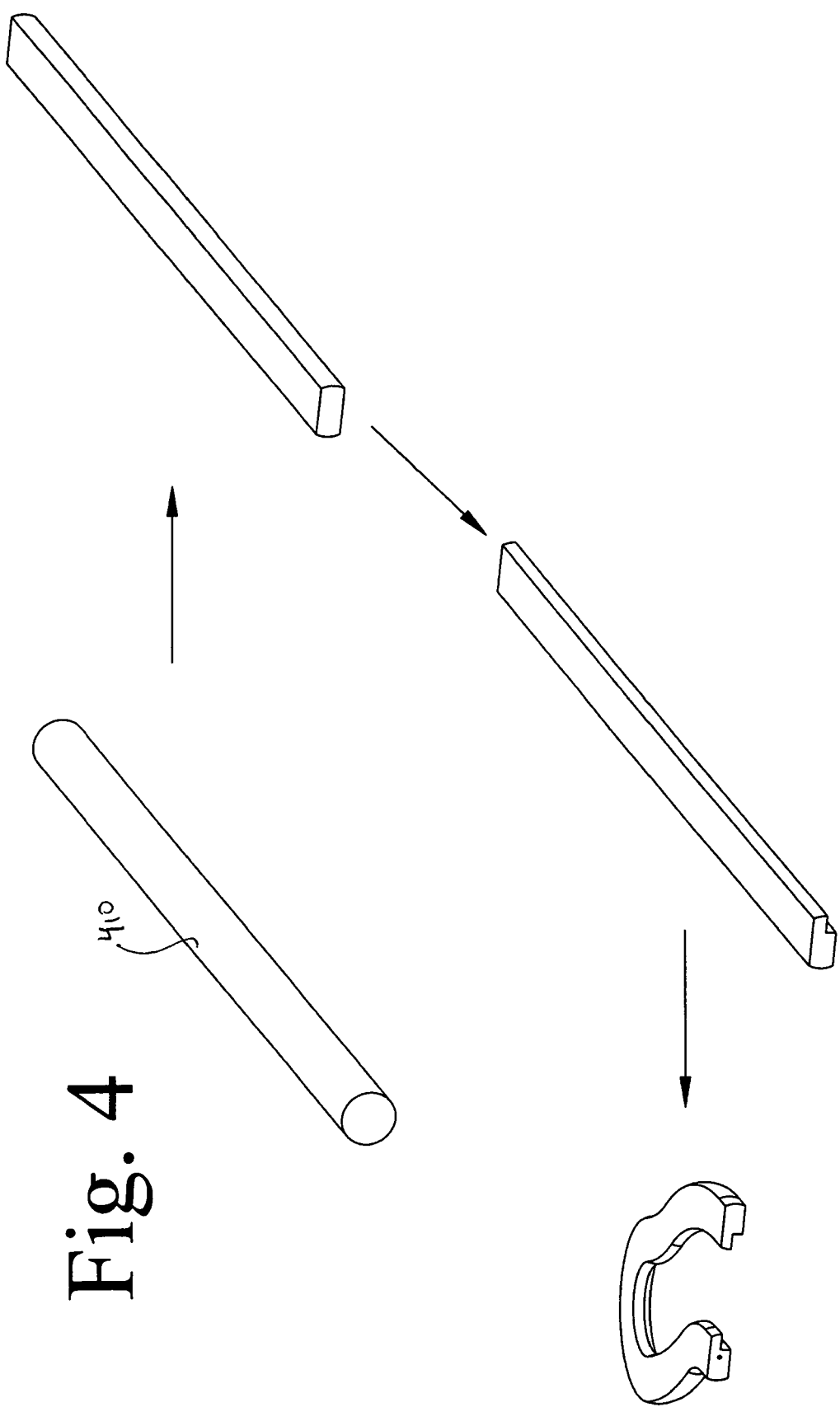

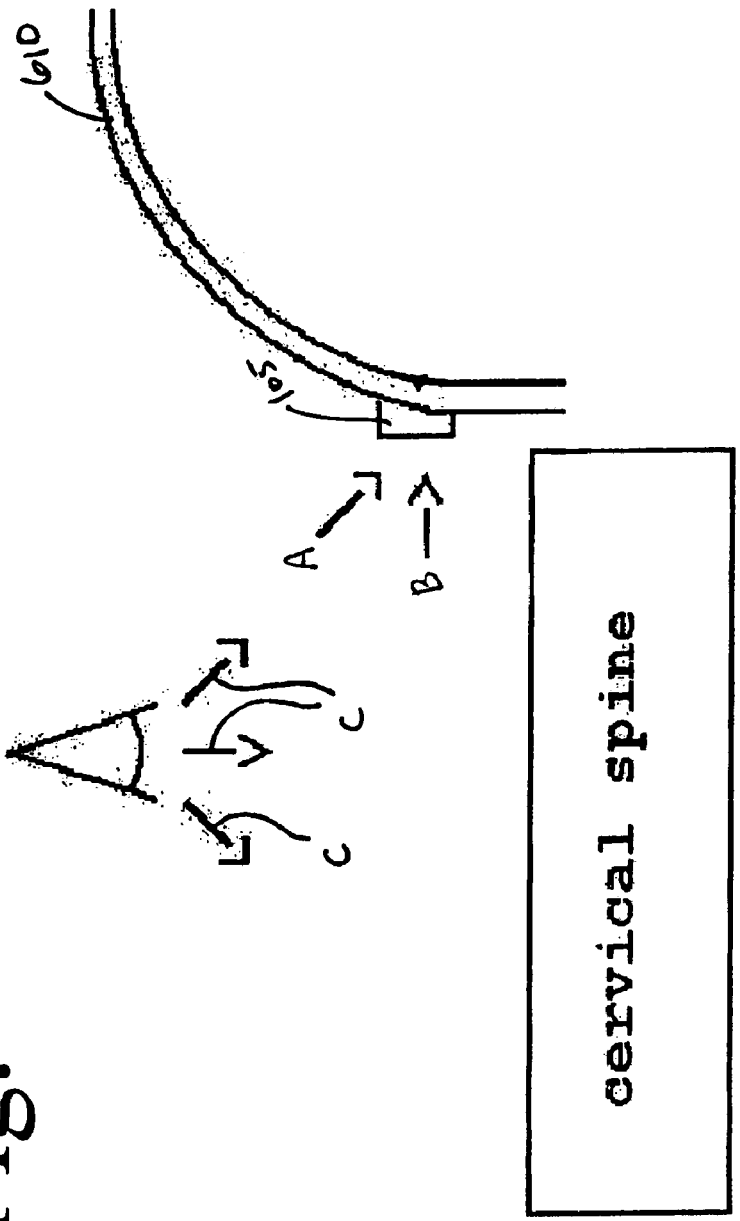

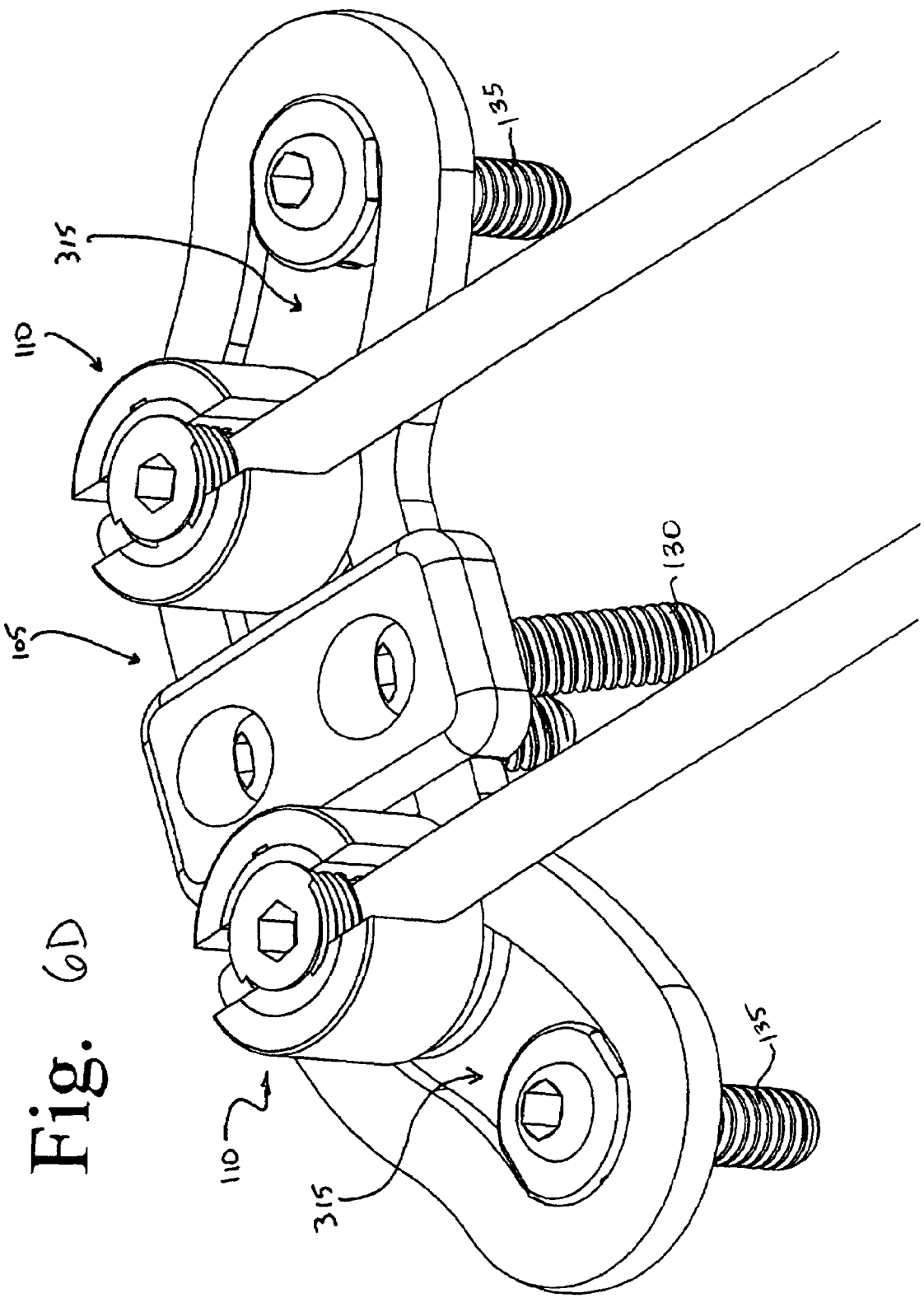

OCCIPITO FIXATION SYSTEM AND METHOD OF USE

REFERENCE TO PRIORITY DOCUMENT

This application claims priority of co-pending U.S. Provisional Patent Application Ser. No. 60/579,531 entitled "An Occipital Fixation System and Method of Use", filed Jun. 14, 2004 and U.S. Provisional Patent Application Ser. No. 60/659,675 entitled "An Occipito-Cervical Fixation System and Method of Use", filed Mar. 7, 2005. Priority of the aforementioned filing dates is hereby claimed and the disclosures of the Provisional Patent Applications are hereby incorporated by reference.

BACKGROUND

The present disclosure relates to bone fixation systems, components thereof, and methods of implant placement. These systems are used to adjust, align and maintain the spatial relationship(s) of adjacent bones or bony fragments after surgical reconstruction of skeletal segments. More specifically, but not exclusively, the present disclosure relates to devices that fixate the skull onto the cervical spine.

Whether for degenerative disease, traumatic disruption, infection or neoplastic invasion, surgical reconstructions of the bony skeleton are common procedures in current medical practice. Regardless of anatomical region or the specifics of the reconstructive procedure, many surgeons employ an implantable bone fixation device to adjust, align and maintain the spatial relationship(s) of adjacent bones or bony fragments during postoperative healing. These devices are usually attached to bone using screws, cables or similar fasteners and act to share the load and support the bone as healing progresses.

The region of articulation between the base of the skull and the upper cervical spine is known as the cranio-vertebral junction. This critical intersection houses and protects the upper aspect of the spinal cord as it emerges from the lower end of the brainstem. Instability of this region can lead to severe spinal cord injury with devastating neurological deficits and death. In order to avoid neurological injury in patients with cranio-vertebral instability, surgical fixation of the hyper-mobile region is performed. Unfortunately, this procedure is technically demanding and the shortcomings of available fixation devices add to the challenge.

SUMMARY

The shortcomings of occipito-cervical fixation devices include:

a) The fixation device is anchored onto the sub-occipital bone in the midline and/or on either side of midline. While bone screws, cables, hooks, clamps and other fasteners have been used, bone screws are used most commonly. In attachment onto the sub-occipital bone, the screws are placed into the underlying bone perpendicular to the bone surface. Unfortunately, this trajectory is in line with the rotational forces acting upon the cranium and screws placed in this way experience maximum load. Further, perpendicular screw placement provides sub-optimal resistance to pull-out since the screws do not capture a wedge of bone as they would with non-perpendicular placement. Lastly, this trajectory is not in line with the surgeon's line of vision—increasing the technical difficulty of screw placement and the likelihood of poor positioning.

b) Extensive contouring is often required so that the fixation device can conform to the complex and tortuous anatomy of this region. The contouring is done at the time of surgery and this step increases the length of the operation. Intraoperative contouring of orthopedic devices is imprecise and devices that are shaped in this way are less likely to conform well to the regional anatomy. This is especially true in regions of tortuous anatomy. Lastly, the contouring process will introduce a variety of curves and stress-risers into the device that may weaken key components. These factors will collectively increase the likelihood of device failure.

In view of the proceeding, it would be desirable to design an improved cranio-vertebral fixation device and placement protocol. An improved device desirably provides superior bone fixation at this critical region while greatly increasing the ease of use and the reliability of the implantation process.

Disclosed is a device that attaches onto the skull. Bone screws are placed through the device and into the underlying bone at an angle that is not perpendicular to the bone surface or at a variety of different angles. Where the screws are placed at a non-perpendicular angle to bone, they can be longer than those screws placed at a right angle. It also means that a wedge of bone is interposed between the screw tip and the bone surface and this wedge would have to be dislodged before the screw can be avulsed from the bone. These factors increase screw resistance to pull-out in a manner independent of screw design. Lastly, screw trajectory can now be placed within the surgeon's line of vision, thereby making the screw placement technically easier and more precise.

An interconnecting member, such as a rod, is used to connect the occipital attachment to the cervical attachment(s). Whereas current art connects these attachments using a rod or plate that requires contouring, the disclosed device uses a multi-axial connector that is freely positionable. This connection allows placement of the inter-connecting rods/plates without contouring and permits rapid and precise device implantation without placement of stress risers within the implanted device. Several embodiments of the connector are shown and described below.

The fixation systems described herein provide ease of use, reliable bone fixation, and optimal biomechanical advantage. The systems also maximize the likelihood of proper device placement and expedite the operative procedure.

In one aspect, there is described a skull-spine connection device, comprising a connector connecting a skull connection device to a spine connection device, wherein the connector permits multi-axial, relative movement between the skull connection device and the spine connection device, and wherein the connector is configured to lock the skull connection device and spine connection device in a predetermined orientation relative to one another.

In another aspect, there is described a skull attachment device, comprising a skull attachment member configured to be attached to a skull; a rod fixation assembly configured to attach a rod to the skull attachment member, comprising an inner saddle member having a ledge configured to engage a lower region of the skull attachment member and an extension that extends upwardly through an aperture in the skull attachment member, the extension having a slot sized to receive the rod; an outer saddle member that concentrically fits over the inner saddle member on an upper region of the skull attachment member, the outer saddle member having a slot that aligns with the slot on the outer saddle member and that receives the rod; and a locking member that engages the inner saddle member above the rod when the rod is positioned in the slots, wherein the locking member provides a force to the rod to secure the rod in the slots.

In another aspect, there is described a fastening button for fastening a device to a bone, comprising a base having an engagement surface for engaging a surface of the bone; and a post extending outwardly from the base, an outer surface of the post configured to engage an edge of a hole in the bone, wherein the post is positioned in an off-center location relative to the base.

In another aspect, there is described a skull fixation assembly, comprising a first bone screw having a shank that extends along an axis, the shank configured to be lodged into a skull, and a skull attachment device having a first borehole for receiving the shank of the bone screw, wherein the bone screw can be mounted in the first hole in a multi-axial configuration such that the axis of the shank can enter the skull at a variety of angles.

The details of one or more embodiments are set forth in the accompanying drawings and the description below. Other features, objects, and advantages will be apparent from the description and drawings, and from the claims.

DESCRIPTION OF DRAWINGS

FIG. 2 shows a perspective view of a portion of the occipito-cervical fixation system in an exploded state.

FIGS. 3A and 3B show top and bottom perspective views, respectively, of an occipital attachment of the system.

FIG. 4 shows exemplary steps for manufacturing the occipital attachment.

FIG. 5B schematically shows an occipital attachment attached to the sub-occipital bone.

FIG. 6D shows a top view of the occipital attachment with rod fixation assemblies positioned medial of bone screws.

Like reference symbols in the various drawings indicate like elements.

DETAILED DESCRIPTION

Figure 1:
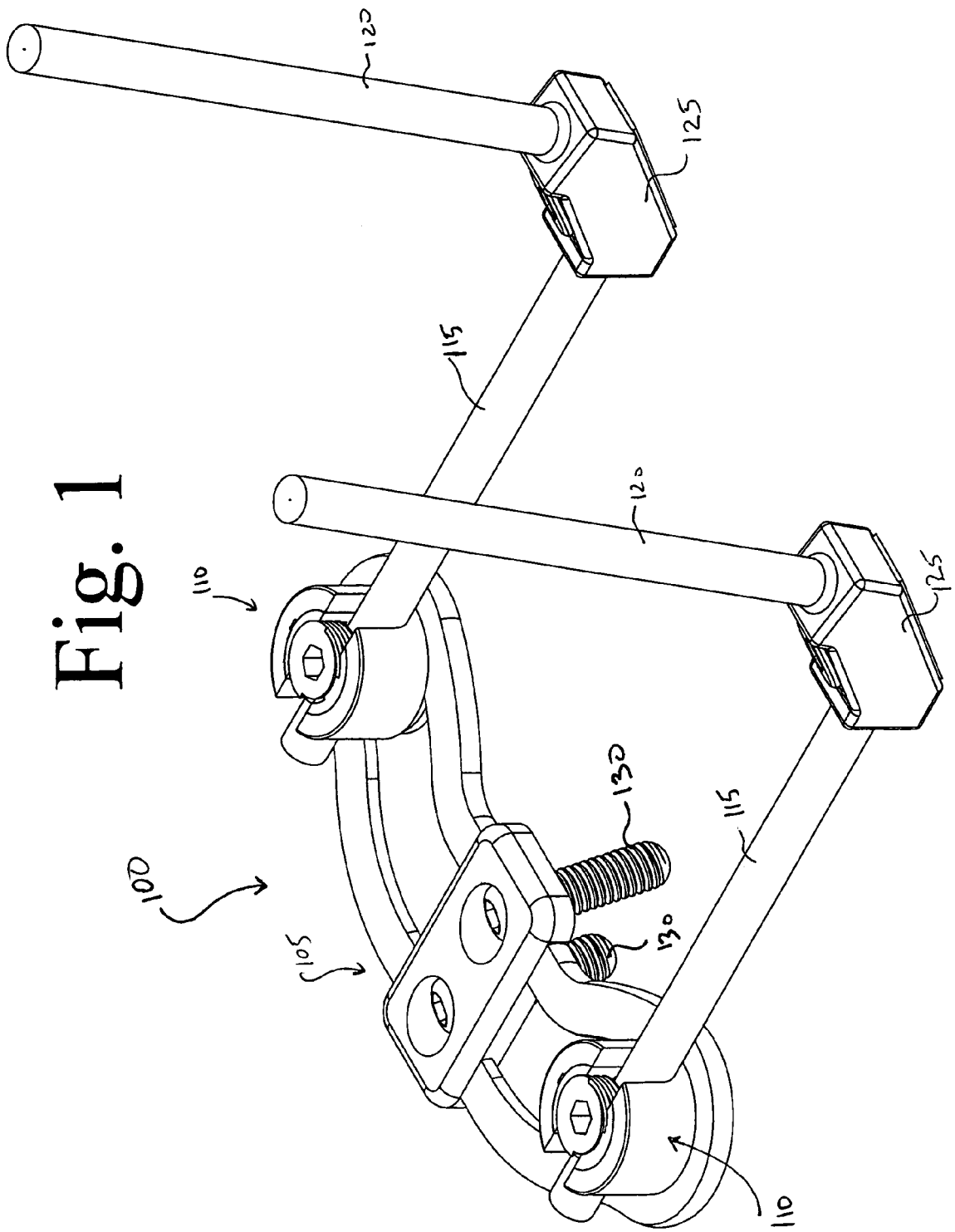
FIG. 1 shows a perspective view of an occipito-cervical fixation system in an assembled state.

FIG. 1 shows a perspective view of an occipito-cervical fixation system 100 in an assembled state. FIG. 2 shows a perspective view of a portion of the occipito-cervical fixation system 100 in an exploded state. The system 100 generally includes an occipital attachment 105, at least one rod fixation assembly 110, at least one skull or occipital interconnecting member comprised of a rod 115, at least one spine or cervical interconnecting member comprised of a rod 120, and at least one multi-axial connector 125. The system 100 further includes one or more bone fasteners, such as bone screws 130, that couple to the occipital attachment 105.

The system 100 is used to interconnect the skull to a portion of the cervical spine. In this regard, the system includes an occipital interconnecting member that connects to the skull and a cervical interconnecting member that connects to the spine. In this regard, the occipital interconnecting member is typically attached to the skull using one or more bone screws and/or an occipital attachment, such as the type described herein. The cervical interconnecting member is typically attached to the spine using one or more bone screws. The interconnecting members can comprise a wide variety of structures, including elongated rods or plates that extend along an axis, as described in detail below.

Occipital Attachment

The occipital attachment 105 is configured to be attached to the skull, such as to the occipital bone of the skull. FIGS. 3A and 3B show top and bottom perspective views, respectively, of the occipital attachment 105, which includes a central body 305 and a pair of curvilinear extensions 310 that extend outwardly from the central body 305. In an embodiment, the extensions 310 are substantially "U" shaped, although the extensions can have a variety of other shapes. The central body 305 includes one or more boreholes 312 for receiving the bone screws 130 (shown in FIGS. 1 and 2). Each borehole 312 is configured such that the respective bone screw is received therein in a poly-axial configuration. Thus, the axis of the shank of the bone screw 130 can be varied to enter the sub-occipital and/or occipital bone at any of a variety of angles. The head of the bone screw and the borehole can have different structures to facilitate the poly-axial configuration.

In one embodiment, the axis of each borehole 312 is angled at a trajectory that facilitates the bone screw entering the bone at angle other than 90 degrees with respect to the surface of the bone. For example, the trajectory of the borehole can be angled relative to the surface of the bone in which the screw is placed. Alternately, the borehole trajectory can be 90 degrees relative to the surface of the bone with a poly-axial screw configuration that permits the bone screw to enter the bone at any of a range of angles.

Each extension 310 extends outwardly from the central body 305 and each defines an aperture 315 that can receive at least one rod fixation assembly 110. (The rod fixation assembly 110 is shown in FIGS. 1 and 2 and described in more detail below.) In one embodiment, the extensions 310 have a curvilinear, rod-like configuration with a flat top surface 320, a flat bottom surface 325, an outer side surface 330, and an elongated indentation 335 on an inner surface. It should be appreciated that the extensions 310 are not required to have the rod-like configuration shown in the drawings.

As shown in FIG. 4, each extension 310 can be manufactured from a cylindrical rod 410 that is machined to have flat surfaces and an internal indentation and then contoured into the final "U" shape or into any desired shape. The extensions 310 are then attached to the central body 305 to form the occipital attachment 105 shown in FIGS. 3A and 3B. Alternately, the occipital attachment 105 can be manufactured as a unitary device with the illustrated shapes rather than separately manufacturing and then attaching the central member and extensions.

It should be appreciated that other types of occipital attachments can be used with the system 100.

Bone Screw Configuration

As mentioned, the occipital attachment 105 is attached to the skull using the bone screws 130 (shown in FIG. 1), which have a head portion that engages the occipital attachment 105 and a shank portion that engages the skull. The boreholes 305 are configured such that the bone screws 130 are polyaxial in that the axis of the bone screw can be varied to approach and enter the bone at a variety of angles. In one embodiment, the boreholes extend along an axis that is angled at a non-perpendicular angle relative to a horizontal plane of the occipital attachment 105. However, the boreholes are not required to extend along an axis that is angled at a non-perpendicular angle relative to a horizontal plane of the occipital attachment 105. The poly-axial bone screw configuration provides a more secure attachment with the underlying bone than if the bone screws were required to enter the bone at a fixed angle, such as at a 90 degree angle. This also permits both bone screws to enter the bone in non-parallel trajectories and in trajectories that are non-perpendicular to the bone surface, although a perpendicular trajectory can be used. The poly-axial configuration also permits the screws to enter the bone along a trajectory that coincides with the surgeon's line of sight and facilitates installment of the occipital attachment.

Figure 5A:
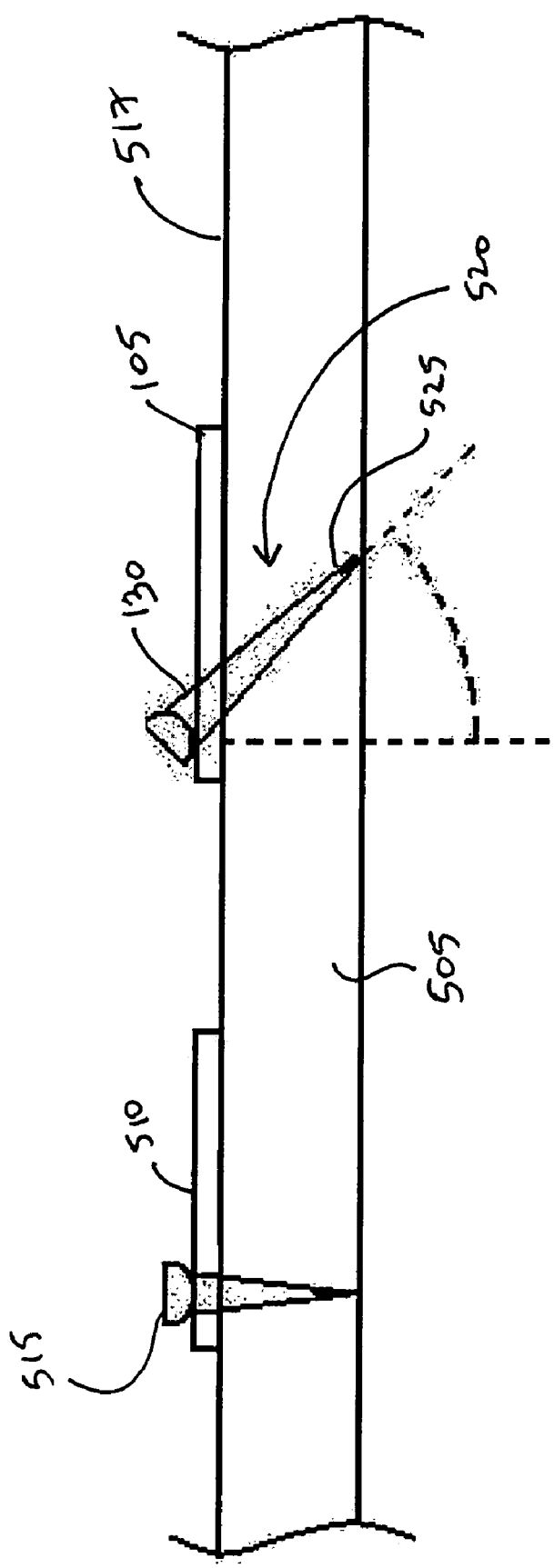
FIG. 5A shows a schematic view of a bone structure attached to two occipital attachments.

This is described in more detail with reference to FIG. 5A, which shows a schematic view of a bone structure 505 attached to two occipital attachments, including the occipital attachment 105 with a poly-axial bone screw 130 and an occipital attachment 510 having a fixed-angled bone screw 515 that enters the bone at a right angle. The "angle" is the angle between an outer surface 517 of the bone structure 505 and a longitudinal axis of the bone screw, such as the longitudinal axis A of bone screw 130. The non-perpendicular angled configuration of the bone screw 130 permits the bone screw 130 to have a longer bone-contact length than the perpendicular bone screw 515. Because the bone screw 130 enters the bone at a non-perpendicular angle, there is additional contact area between the bone screw 130 and the bone structure 505, thereby providing a more secure attachment. Thus, since the screws are not placed perpendicular to bone, longer bone screws may be used for any given bone thickness. As mentioned, the entry angle of the bone screw 130 can be varied due to the poly-axial configuration of the bone screw. The borehole itself can have a trajectory that facilitates a particular entry angle into the bone.

Moreover, a wedge-shaped region 520 of bone is interposed between a distal tip 525 of the screw 130 and the bone surface 517. The wedge-shaped region 520 would have to be dislodged before the angled screw 130 can be avulsed from the occipital bone. These two factors work synergistically to significantly increase screw resistance to pull-out in a manner independent of screw design.

An additional advantage of the poly-axial bone screw configuration is described with reference to FIG. 5B, which schematically shows an occipital attachment 105 attached to the sub-occipital bone 610. The axial trajectory of a poly-axial bone screw is represented by the arrow labeled "A". This bone screw enters the bone at a downward angle (relative to FIG. 5B) that is non-perpendicular to the bone. The axial trajectory of a bone screw that enters the bone at a right angle is represented by the arrow labeled "B" in FIG. 5B. In addition, the surgeon's typical lines of vision during surgery are also shown and labeled C in FIG. 5B. The bone screw with the trajectory A is more inline with the surgeon's line of vision than the bone screw with the trajectory B. This makes the procedure technically easier and decreases the likelihood of incorrect screw placement. It should be appreciated that where the occipital attachment includes more than one bone screw, the trajectory of the placed screws are not necessarily parallel to one another. This provides a "crossed-screw" configuration and forms an additional wedge of bone between the screw shafts, wherein the wedges must be dislodged for screw pull-out, thereby further strengthening the fixation of the occipital attachment to the bone.

Figure 6A:
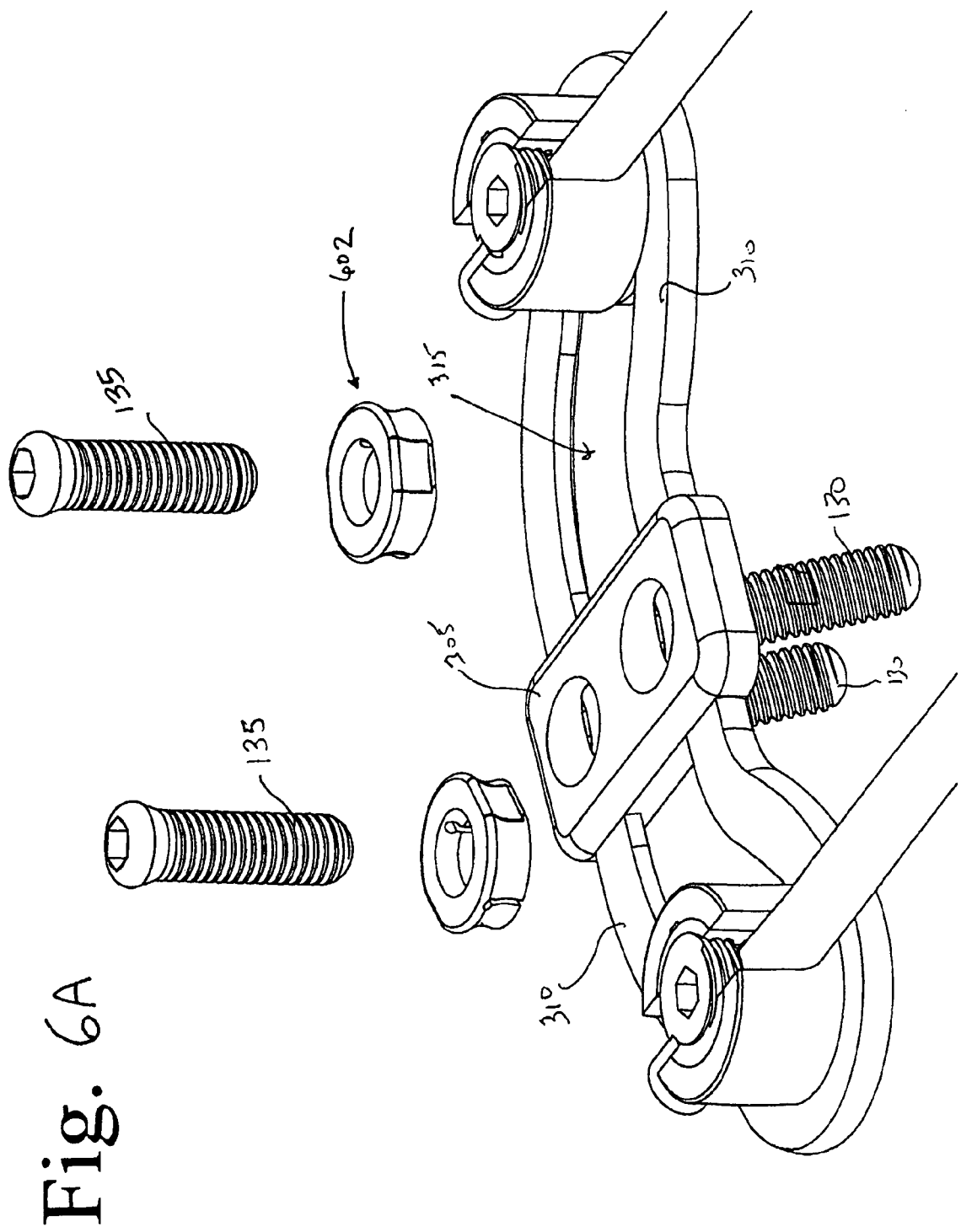
FIG. 6A shows the occipital attachment coupled to bone screws via a coupler.
Figure 6B:
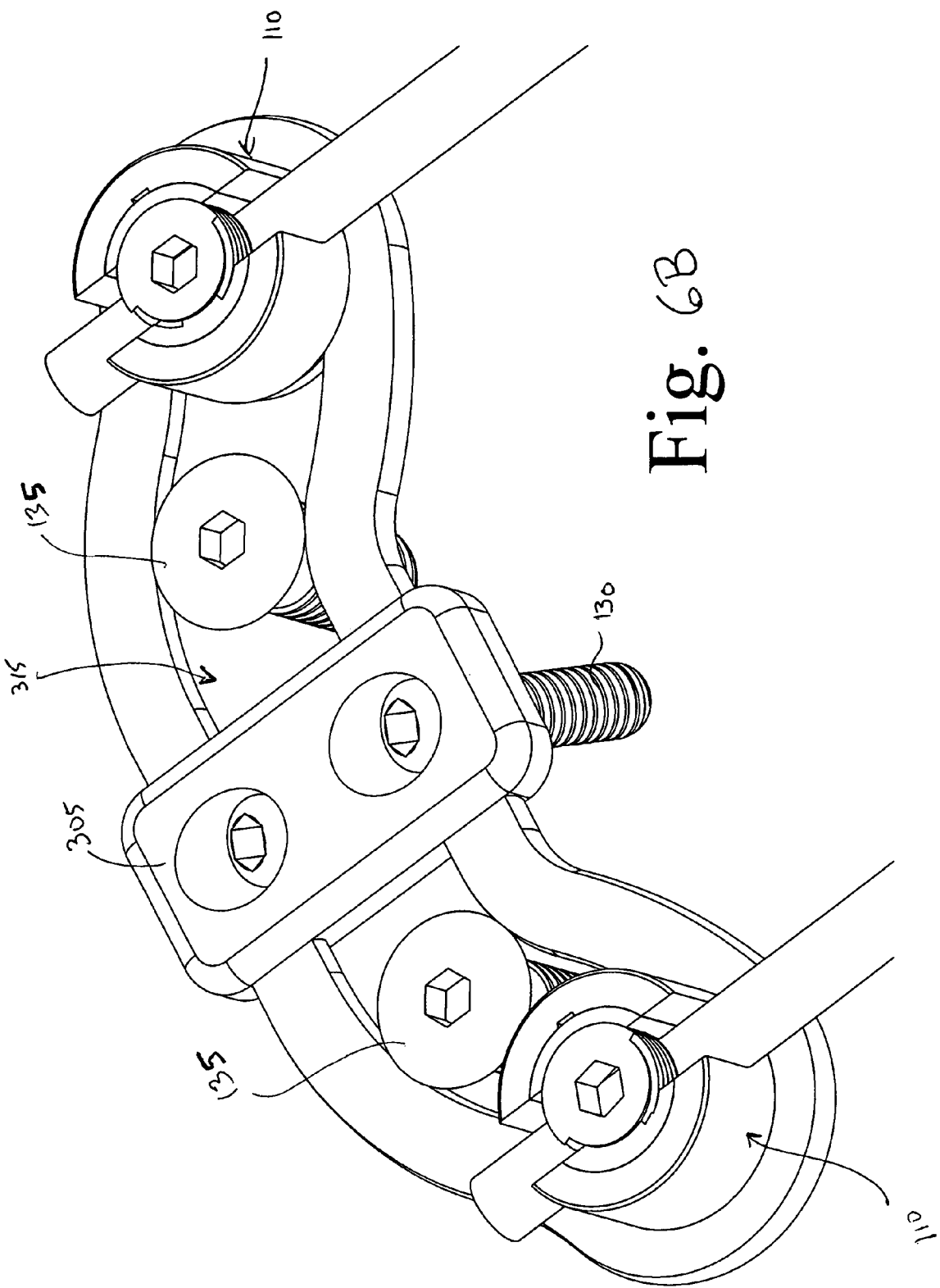
FIG. 6B shows the occipital attachment coupled directly to additional bone screws.

With reference to FIGS. 6A and 6B, one or more additional bone screws 135 can be inserted through the aperture 315 and coupled to the occipital attachment 105. The additional bone screws 135 engage the extensions 310 rather than the central member 305 of the occipital attachment 105. As shown in FIG. 6A, each screw can be positioned through a collapsible adapter 602 that is sized and shaped to receive the bone screw 135 and to engage the u-shaped extensions 310. Alternately, the bone screws 135 can directly engage the extensions 310 through the aperture 315, as shown in FIG. 6B.

The additional bone screws can be oriented such that the axes of the additional bone screws are positioned perpendicular to the bone surface or at an angle that is different than the axes of the bone screws 130 in the central body 305. This permits the bone screws 130 in the central body 305 to have a first trajectory with the bone surface, while the bone screws 135 through the aperture 315 have a different trajectory with the bone surface. Indeed, it should be appreciated that the poly-axial configuration of the bone screws permits the bone screws 130 and 135 to all have different trajectories through the bone such that none of the screws are aligned on a parallel trajectory or only some of the screws are aligned on a parallel trajectory.

Figure 6C:
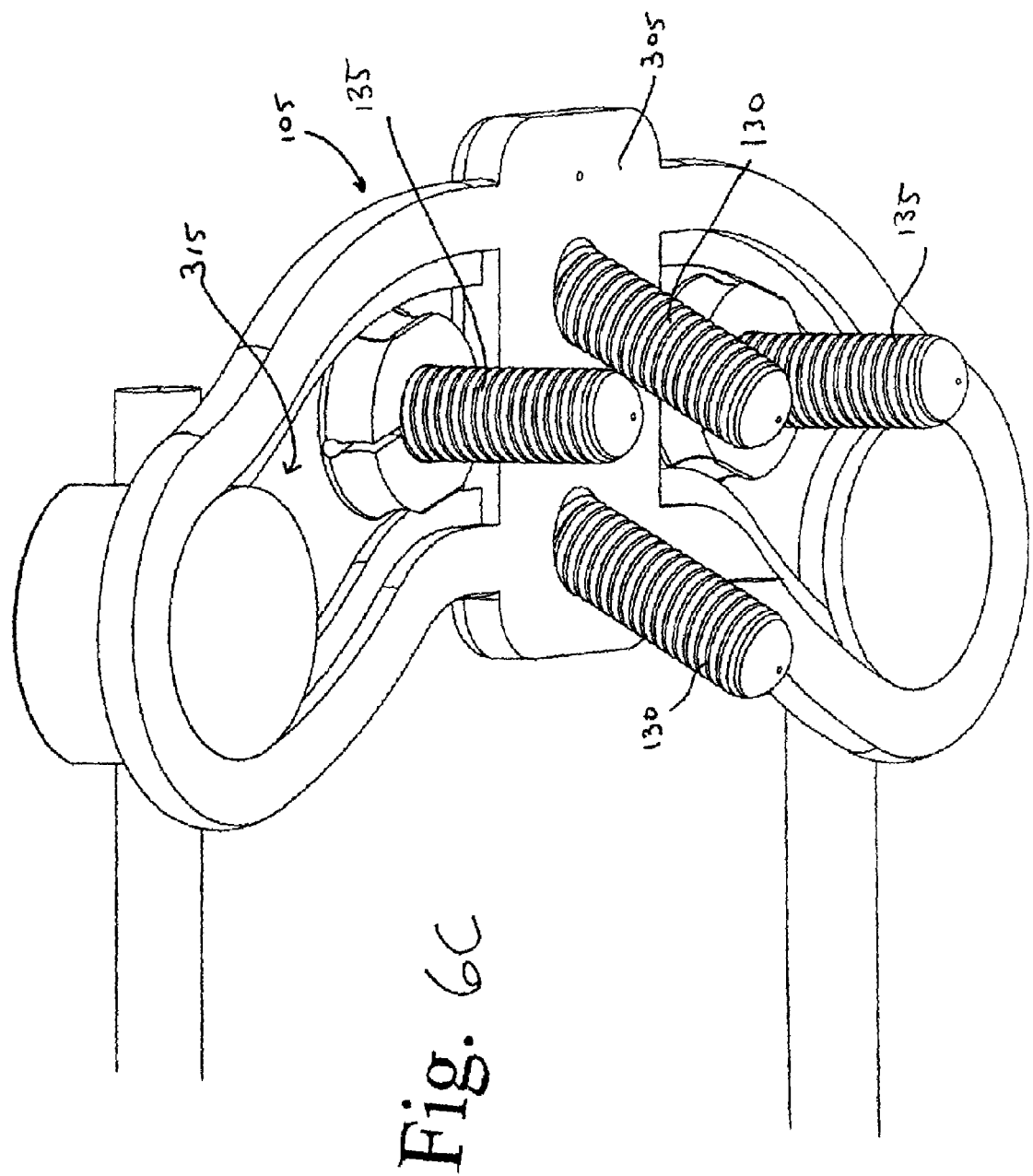
FIG. 6C shows a bottom view of the occipital attachment with a cross-screw configuration.

FIG. 6C illustrates how the bone screws 130 central body 305 and the bone screws 135 through the apertures 315 can have different trajectories to provide a "crossed screw" configuration that can significantly increase pull-out strength and reduce the likelihood of screw loosening and device migration. While a particular screw configuration is shown, the cross-screw configuration can be achieved by using various combinations of screw trajectories for the screws. For example, the screws 130 in the central body 305 can have a perpendicular trajectory through the bone while the screws 135 through the aperture 315 are a non-perpendicular trajectory through the bone.

As shown in FIGS. 6B and 6D, the rod-fixation assemblies 110 can be positioned at various locations along the aperture 315 relative to the bone screws 135 in the aperture 315. That is, the rod fixation assemblies 110 are movable to various locations within the aperture 315. Thus, the bone screws 135 can be positioned through the apertures 315 between the rod fixation assemblies 110 and the central body 305 (medial to the rod fixation assembly 110, as shown in FIG. 6B), or on the other side of the rod fixation assembly 110 (lateral to the rod fixation assembles 110, as shown in FIG. 6D.) The lateral positions of the bone screws provides great stability to the system shown in FIG. 6D.

Rod Fixation Assembly

Figure 7:
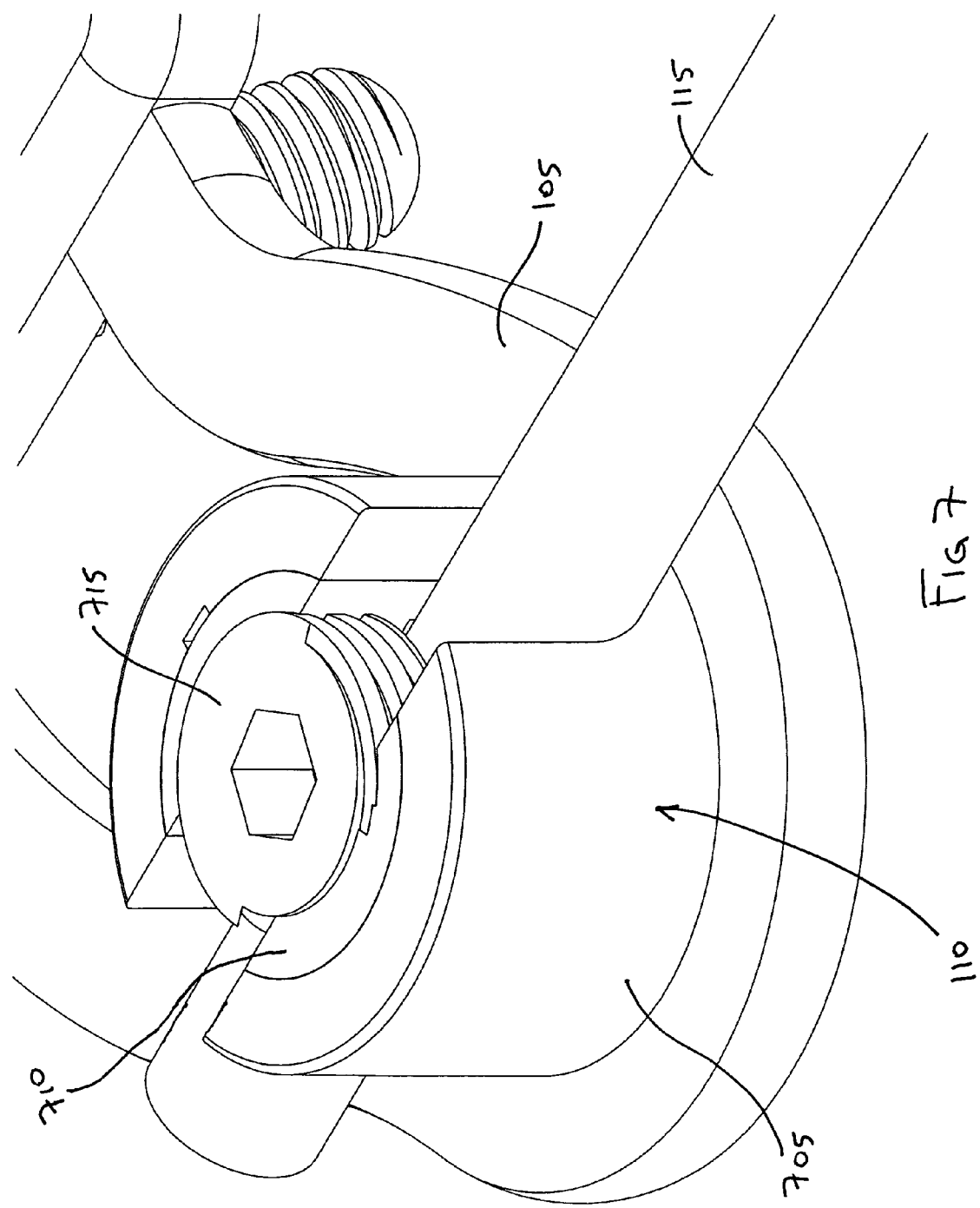
FIG. 7 shows an enlarged view of the rod fixation assembly.

FIG. 7 shows an enlarged view of the rod fixation assembly 110, which removably secures the occipital rod 115 to the occipital attachment 105. As mentioned, the system 100 includes one or more rod fixation assemblies 110 that at least partially fit within the apertures 315 in the occipital attachment 105 and that couple the occipital rod 115 to the occipital attachment 105. With reference to FIGS. 2 and 7, the rod fixation assemblies 110 each include an outer saddle member 705, an inner saddle member 710, and a locking nut 715.

Figure 8A:
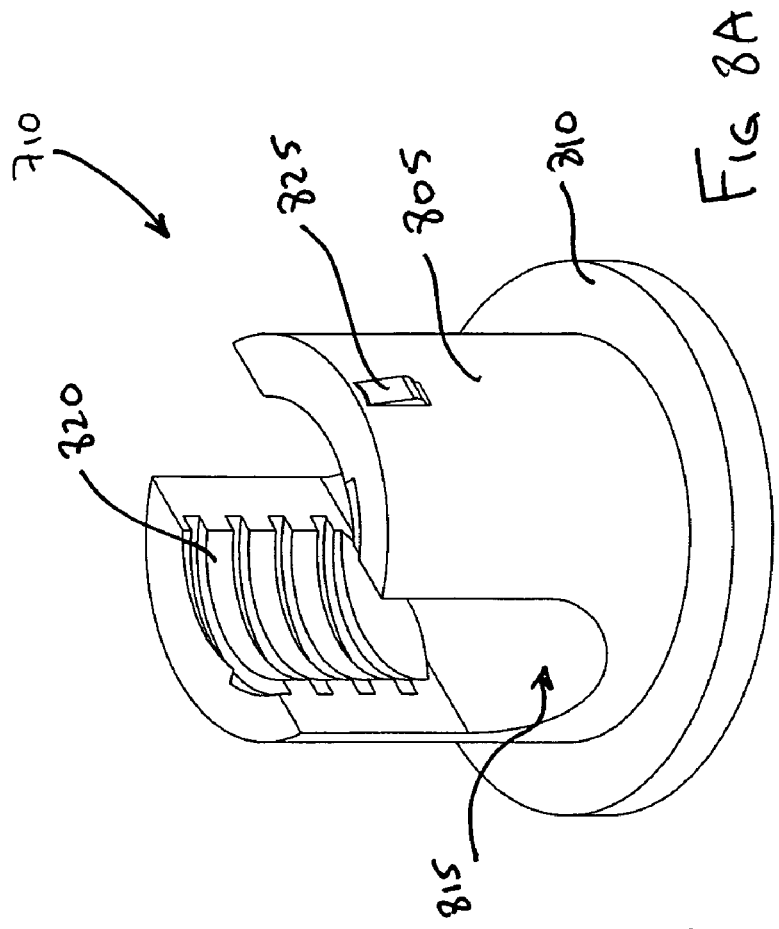
FIGS. 8A and 8B shows a perspective and a side view of an inner saddle member of the rod fixation assembly.
Figure 8B:
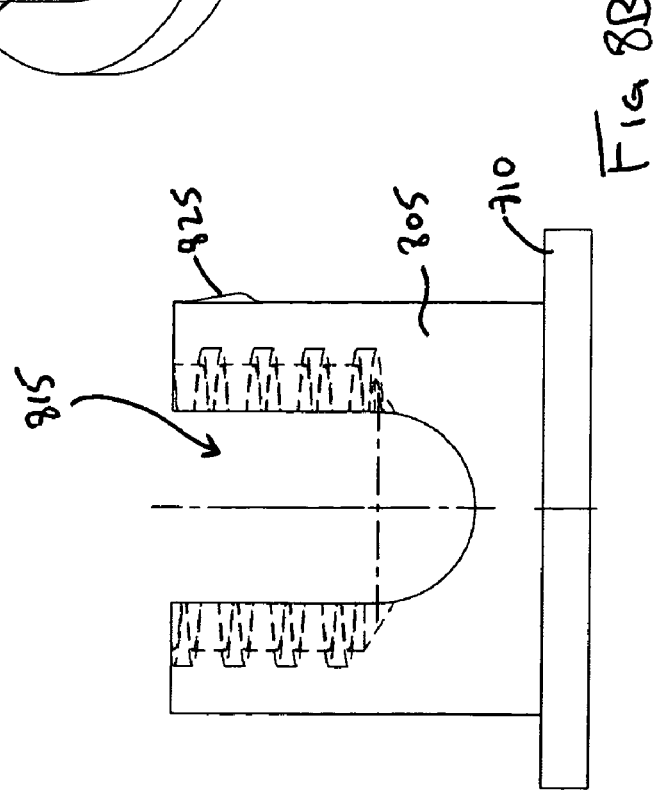

FIGS. 8A and 8B shows a perspective and side views of the inner saddle member 710 of the rod fixation assembly 110. The inner saddle member 710 includes a cylindrical extension 805 that extends upwardly from a base having an annular ledge 810. The extension 805 is sized to fit through the aperture 315 in the occipital attachment 105, although the ledge 810 has a transverse dimension that is larger than the dimension of the aperture 315. The transverse dimension of the ledge 810 is sized to sit within the indentation 335 (shown in FIG. 3B) on the inner surface of the occipital attachment 105.

A slot 815 is formed within the extension 805 for receiving the occipital rod 115. Threads 820 are disposed in an inner aspect of the extension 805 for mating with corresponding threads of the nut 715. In addition, at least one protrusion 825 is located on an exterior surface of the extension 805. The protrusion(s) 825 mate with corresponding indentation(s) in the outer saddle member 705, as described more fully below.

Figure 9A:
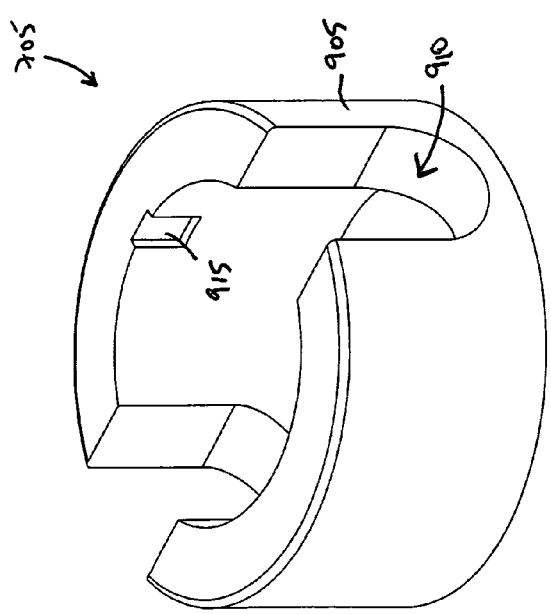
FIGS. 9A and 9B shows a perspective and a side view of an outer saddle member of the rod fixation assembly.
Figure 9B:
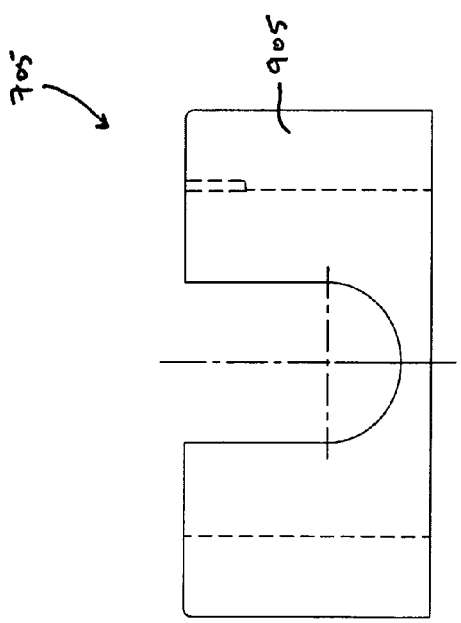

FIGS. 9A and 9B shows perspective and side views of the outer saddle member 705 of the rod fixation assembly 110. The outer saddle member 705 includes a cylindrical wall 905 having a slot 910 extending therethrough. At least one indentation 915 is disposed on an inner surface of the wall 905 and is positioned to mate with the protrusion 825 of the inner saddle member 710 when the inner saddle member 710 and the outer saddle member 705 are coupled to one another.

Figure 10:
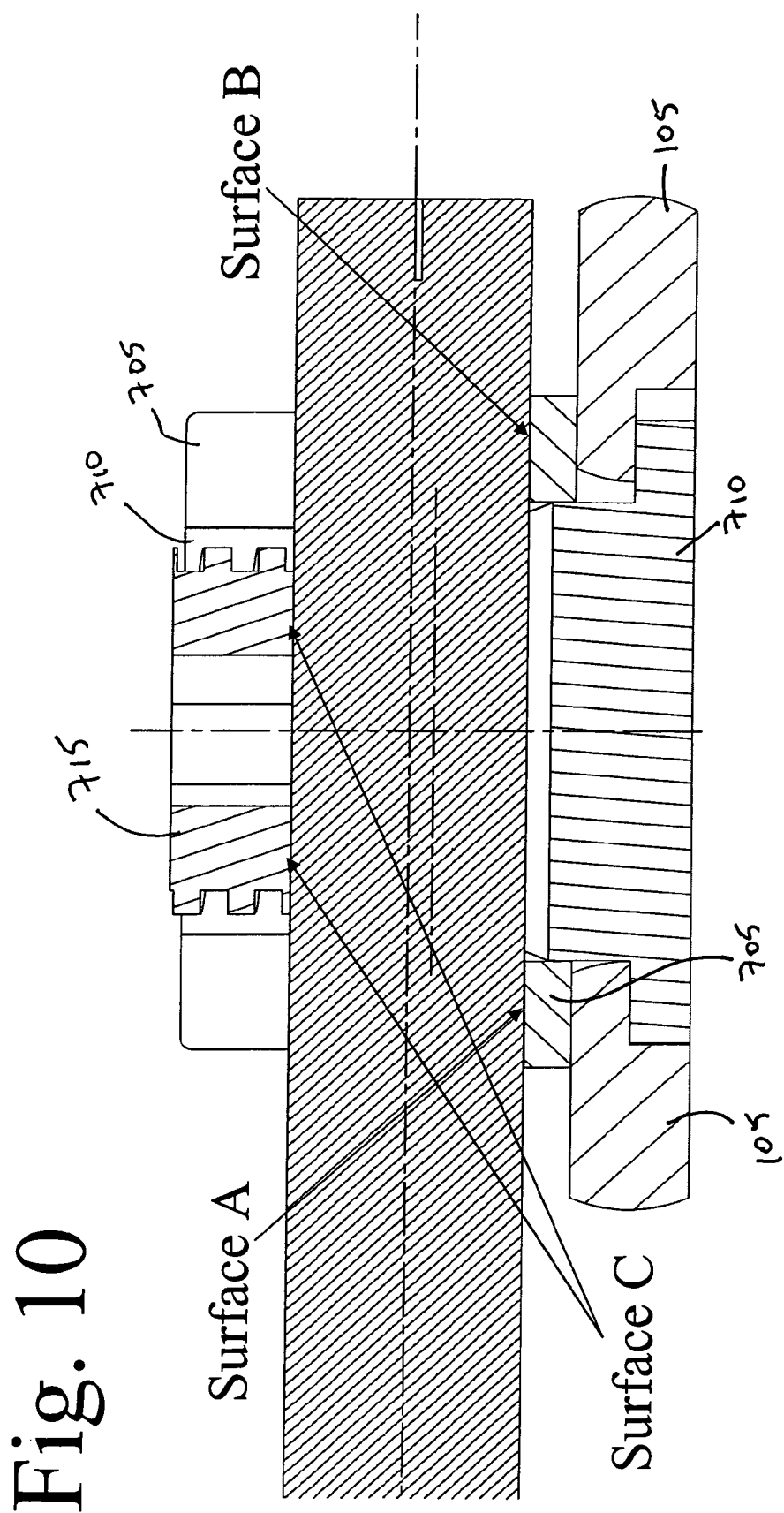
FIG. 10 shows a cross-sectional view of the rod fixation assembly in an assembled state and attached to the occipital rod and the occipital attachment.

FIG. 10 shows a cross-sectional view of the rod fixation assembly 110 in an assembled state and attached to the occipital rod 115 and the occipital attachment 105. The inner saddle member 710 is co-axially positioned within the outer saddle member 705 with the occipital attachment 105 positioned therebetween. The locking nut 715 is positioned within the inner saddle member 710 such that the threads on the nut engage the threads in the inner saddle member 710. The locking nut 715 secures the occipital rod 115 in place. With the locking nut 715 seated, the occipital rod 115 is held in place by three contact surfaces A, B, and C. The bottom of the opening slot within the inner saddle member 710 is lower than the corresponding opening slot within the outer saddle member 705 such that the lower surface of the occipital rod 115 contacts the outer saddle member at surfaces A and B. The upper surface of the occipital rod 115 contacts the lower surface of the locking nut 715 along surface C.

Figure 11:
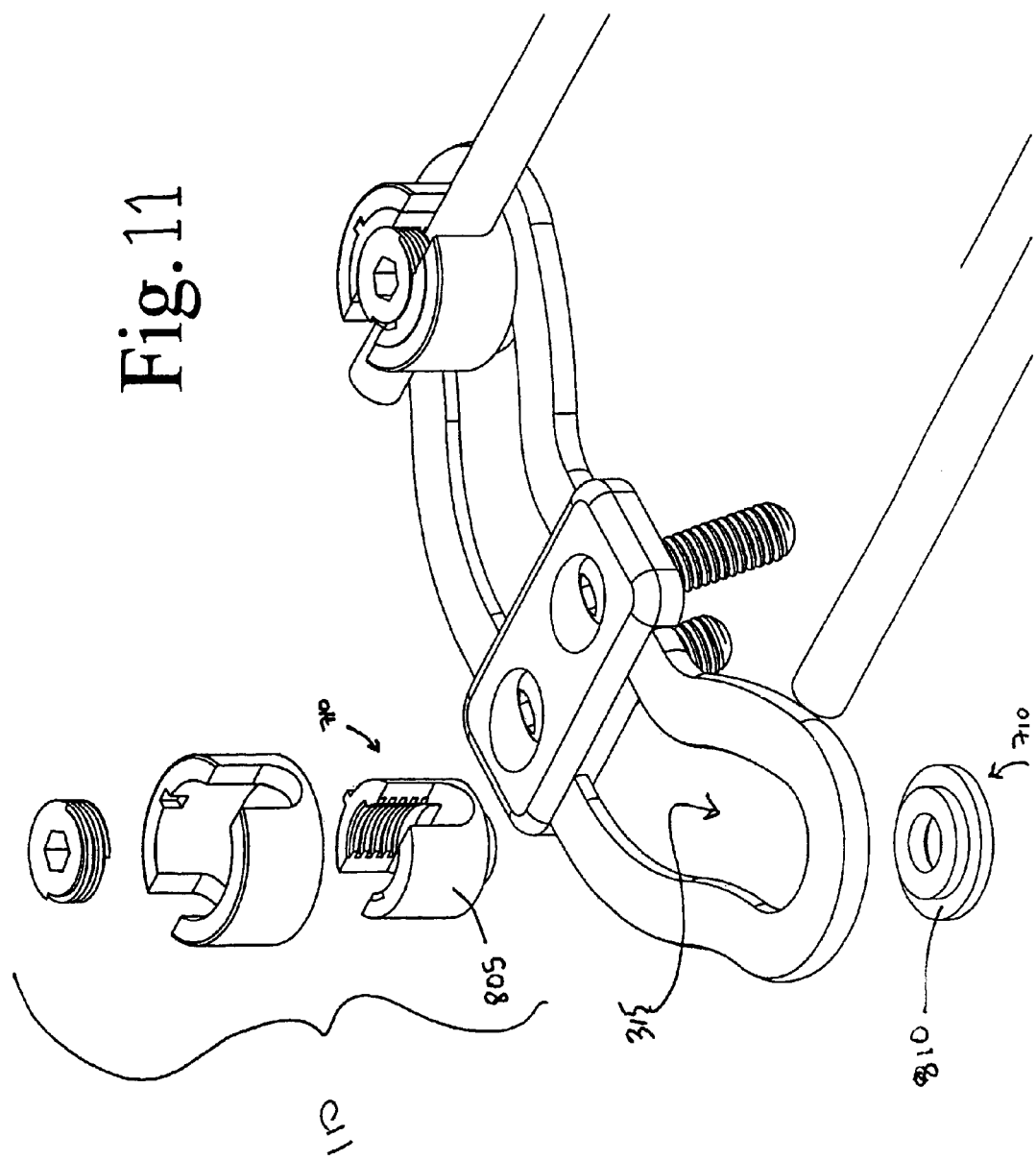
FIG. 11 shows an alternative embodiment of the rod fixation assembly.

FIG. 11 shows an alternative embodiment of the rod fixation assembly 110 wherein the inner saddle member 710 includes a plurality of segments or portions. The cylindrical extension 805 and the ledge 810 comprise two separate pieces that mate together to collectively form the inner saddle member 710. Using this design, the aperture 315 of the occipital attachment 105 can be made smaller than that needed to accommodate inner saddle member 710.

The disclosed rod fixation assembly is of great utility. It permits rapid and precise placement of interconnecting rods without the extensive contouring required in current art. It minimizes the introduction of stress risers that are necessarily formed by rod contouring and that can weaken the interconnecting rod. It also allows the connection of the cervical and occipital attachments without pre-load and avoids the placement of un-wanted pull-out forces onto the attachment anchors (screws, etc.). These factors will collectively provide a construct of greater strength and stability. Moreover, since the risk of infection and other peri-operative morbidity is directly related to the length of operation, and because the assembly simplifies and expedites the operative procedure, the overall operative risk to the patient is reduced.

Locking Bone Screws

In the previously described embodiments, such as shown in FIGS. 1 and 2, the bone screws 130 are freely positioned in the bore holes 310 of the central body 305 of the occipital attachment 105. That is, the bone screws 130 freely pass through the bore holes 310 and engage the underlying bone structure but do not lock into the central body 305. In another embodiment, shown in FIGS. 12-14, one or more of the bone screws comprise locking screws 1210 that engage with and lock into the central body 305.

Figure 12:
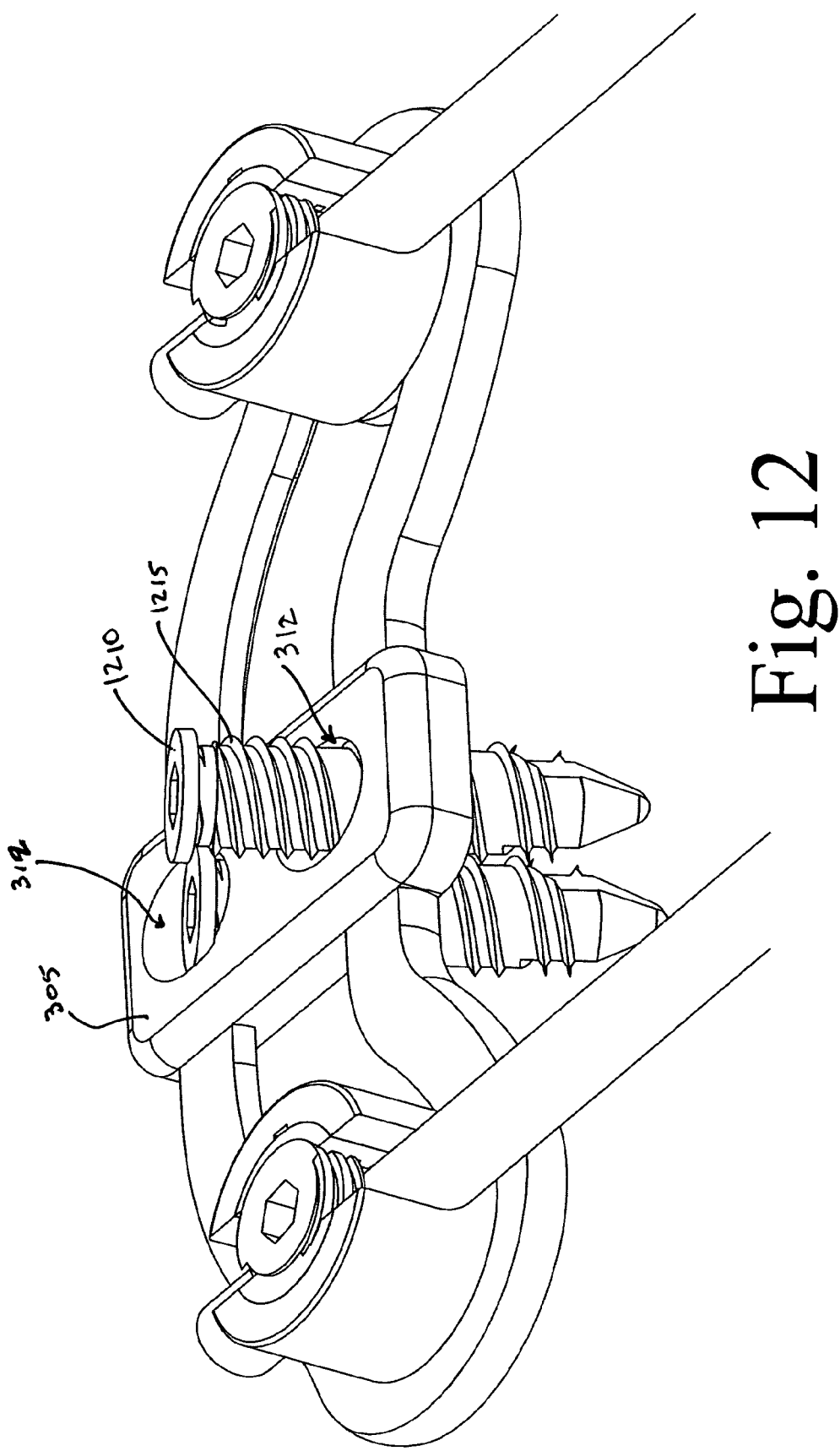
FIGS. 12-14 show embodiments of the occipital attachment wherein one or more of the bone screws engage with and lock into the occipital attachment.

With reference to FIG. 12, in one embodiment the locking bone screws 1210 include a set of threads 1215 that engage corresponding threads located in the bore holes 312 of the central body 305. Thus, as the bone screws 1210 are driven into the underlying bone, the threads 1215 engage with and lock with the threads in the boreholes 312 of the central body 305.

Figure 13:
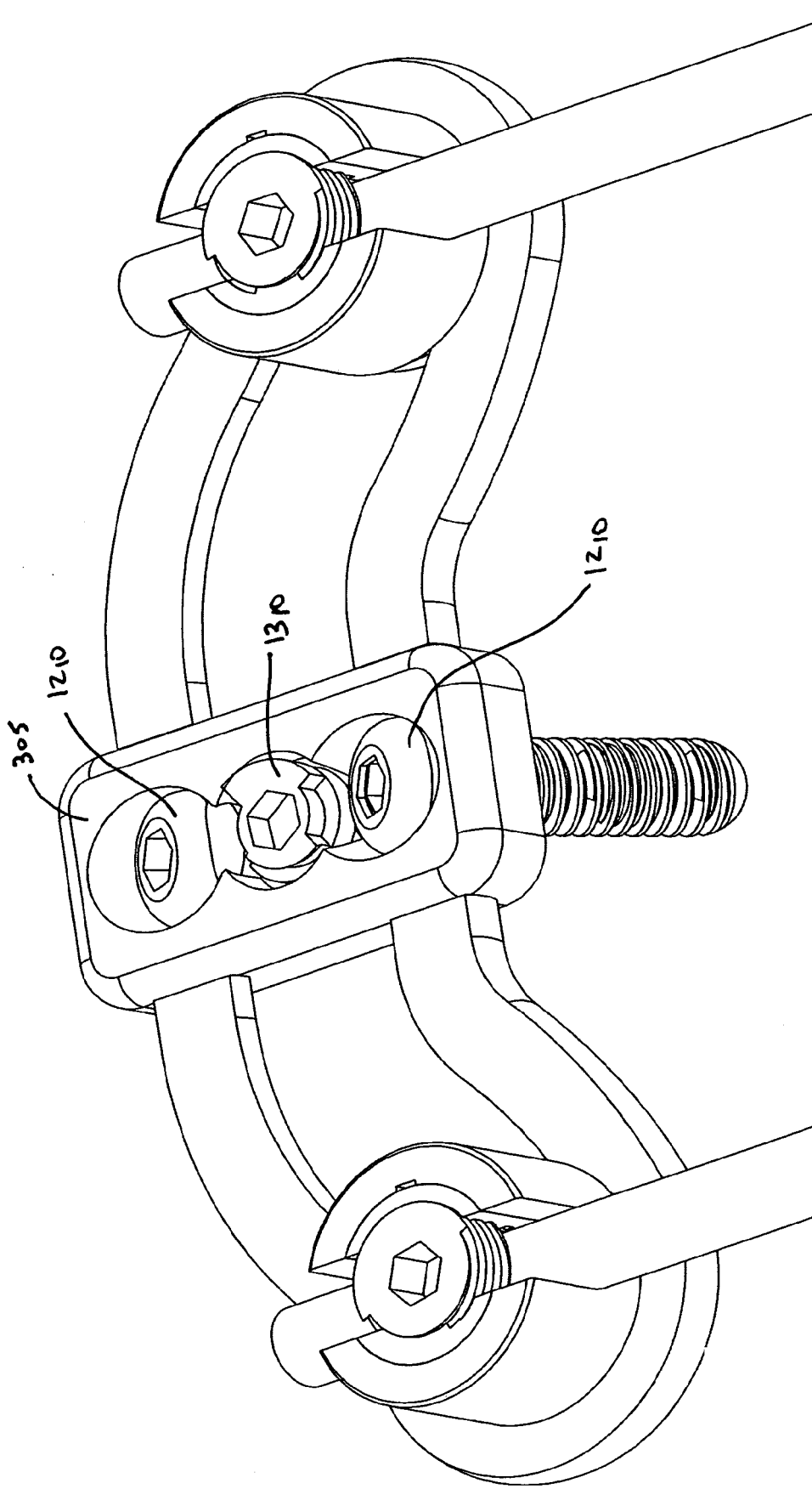
Figure 14:
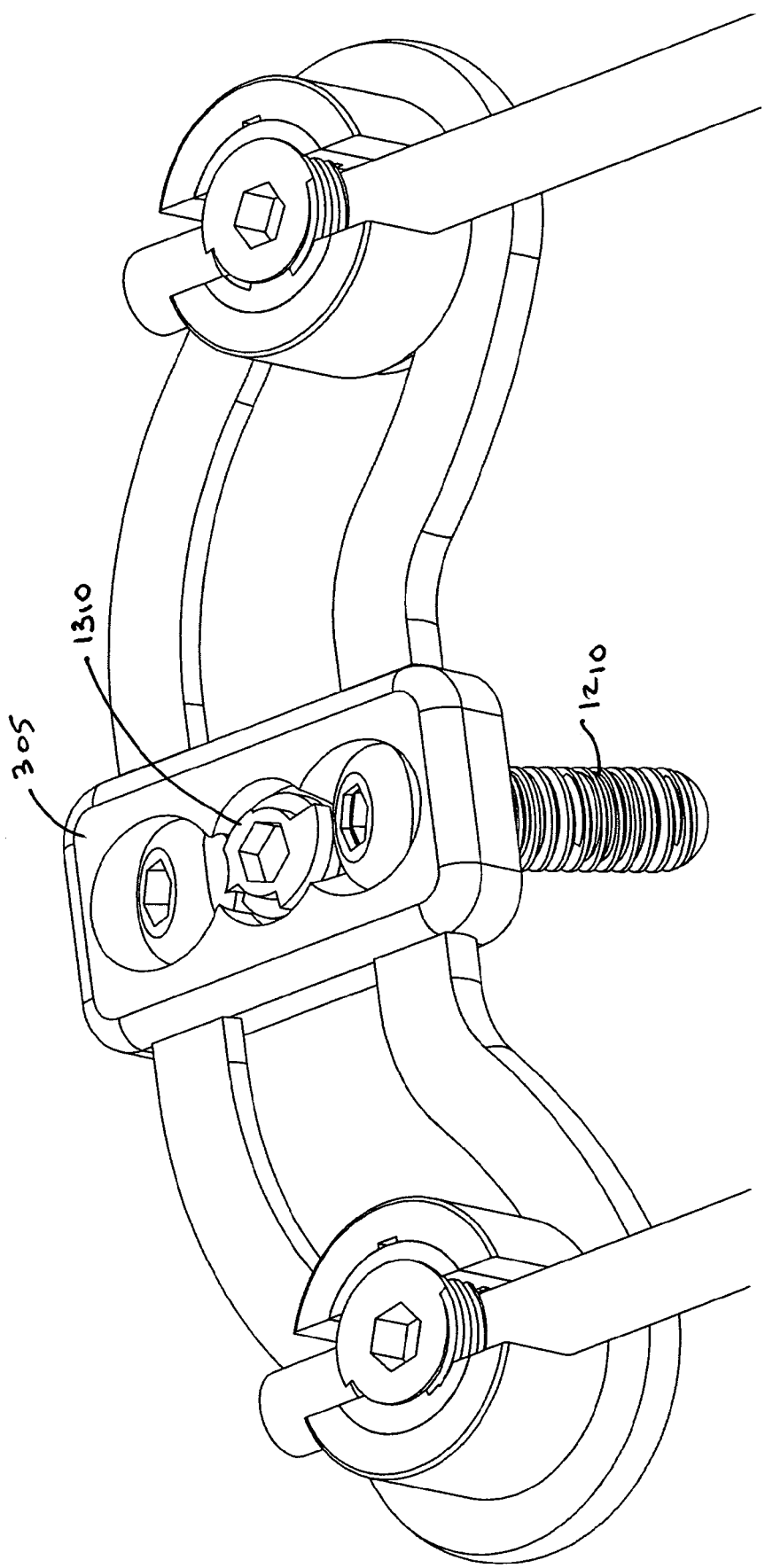

FIGS. 13 and 14 show another embodiment of locking bone screws 1210 that lockingly engage a locking component 1310 positioned in the central body 305. The locking component 1310 can be used to retain and lock the locking screws 1210 after they are fully seated in the bone and the central body 305. In the illustrated embodiment, the locking component 1310 includes a cam-shaped head that can be positioned between an unlocked position (shown in FIG. 13) and a locked position (shown in FIG. 14). In the locked position, the head of the locking component 1310 lockingly engages the locking screws 1210 to prevent the screws from being removed from the bone. In the unlocked position, the locking component 1310 is disengaged from the locking screws 1210 such that the screws can be loosened and removed from the bone. The cam-shaped locking component is rotated to move it between the locked and unlocked positions.

It should be appreciated that there are numerous known mechanisms through which the screws can be locked to a central body 305 after engaging the underlying bone. These include, but are not limited to, the methods and devices described in U.S. Pat. Nos. D440311S, D449692S, 5,364,399, 5,549,612, 5,578,034, 5,676,666, 5,681,311, 5,735,853, 5,954,722, 6,039,740, 6,152,927, 6,224,602, 6,235,034, 6,331,179, 6,454,769, 6,599,290, 6,602,255, 6,602,256, 6,626,907, 6,652,525, 6,663,632, and 6,695,846. This is not an exhaustive listing and many other screw retention methods have been developed and illustrated. It is understood that one of ordinary skill in the art can apply the locking screw mechanisms of the aforementioned patent documents to the device disclosed in this application.

Button Attachments

Figure 15A:
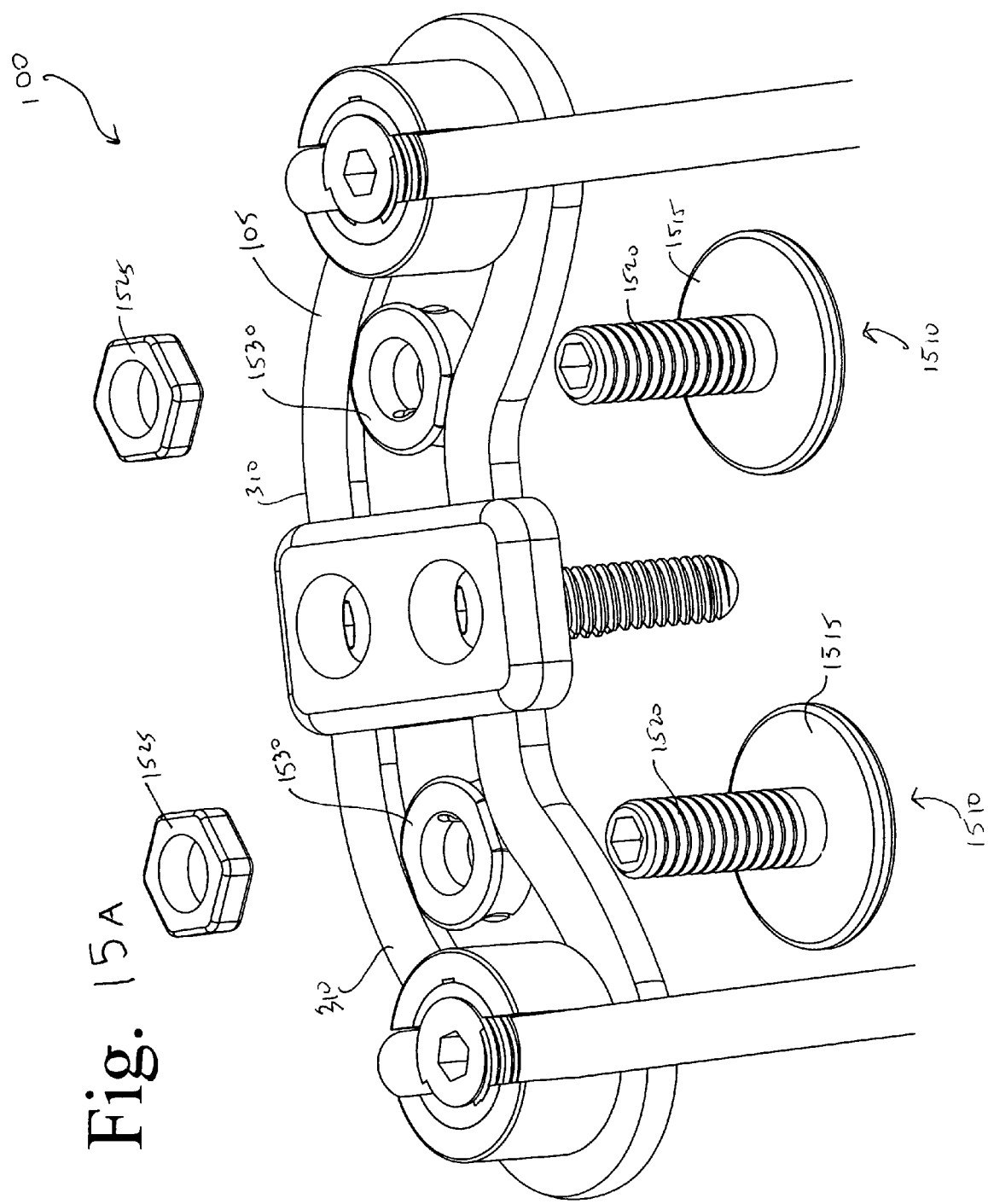
FIGS. 15A shows an embodiment of the system that includes one or more button attachments

FIG. 15A shows an embodiment of the system 100 that includes one or more button attachments 1510 having a base 1515 and attached to an upwardly-extending post 1520 centrally positioned on the base 1515. The button attachment 1510 may be placed through a burr hole into the sub-occipital skull and provide an additional method of fixation for the occipital attachment 105. The base 1515 engages the skull and the posts 1520 engage the occipital attachment 105 using one or more couplers 1530. The couplers 1530 are sized to engage the extensions 310 of the occipital attachment 105 and are secure to the posts 1520 using a locking component, such as a nut 1525.

Figure 15B:
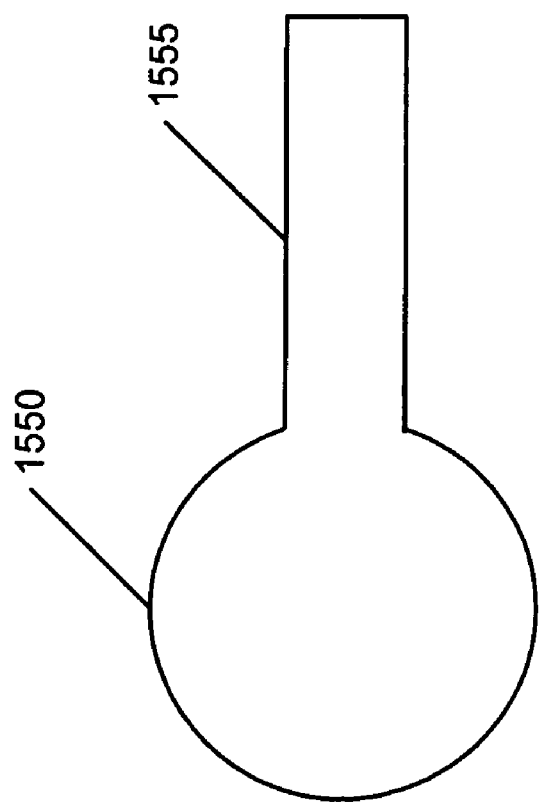
FIG. 15B shows a keyhole-shaped hole that is formed in a bone structure for coupling to a conventional button attachment.
Figure 16:
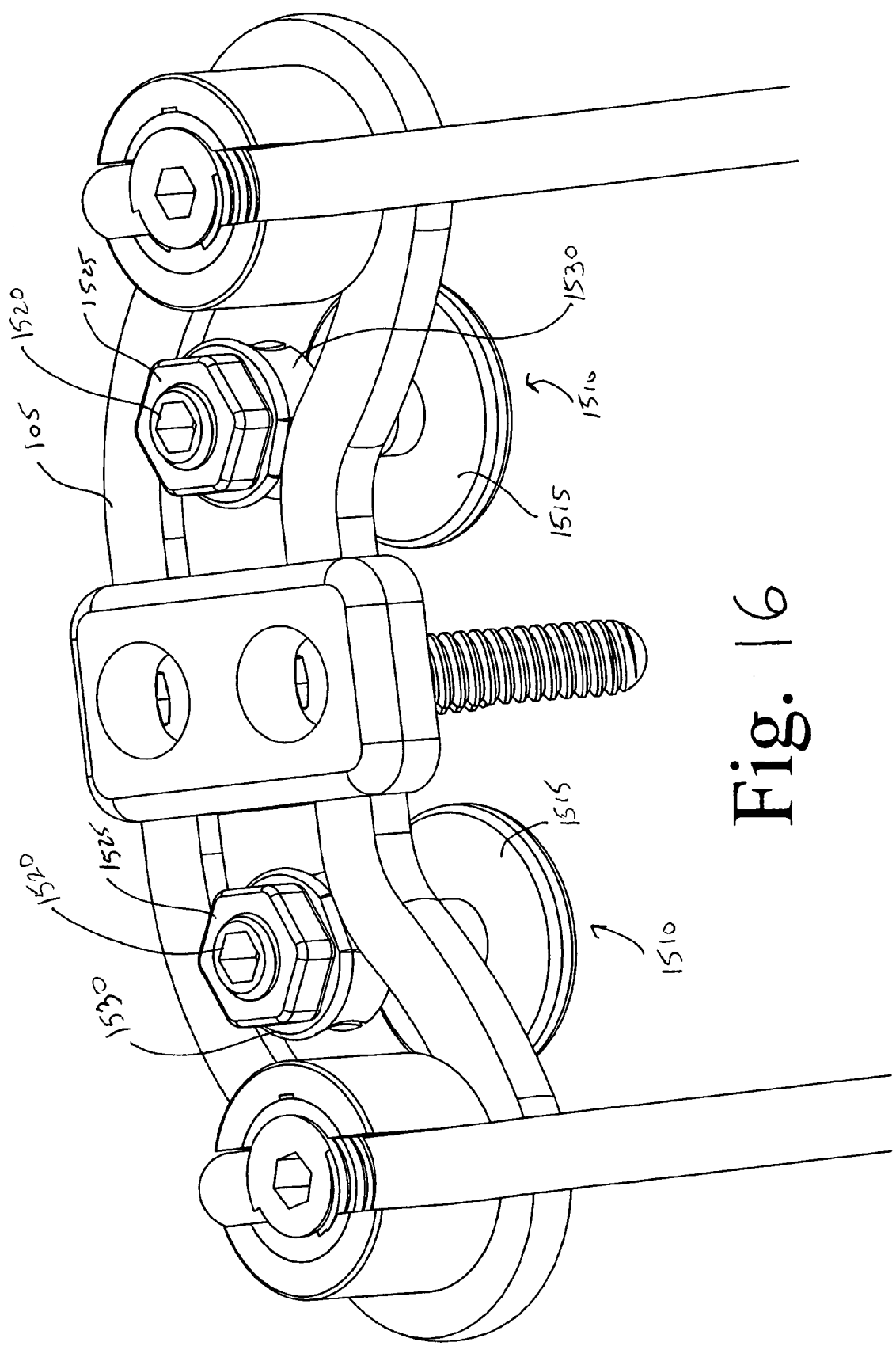
FIGS. 16 show the system that includes one or more button attachments attached to the occipital attachment.

Pursuant to a conventional button-attachment procedure, a "keyhole" shaped hole slightly larger than the base 1515 of the button is made in the bone. The hole is "keyhole" shaped in that the hole has a circular portion 1550 and a slot portion 1555 that extends outwardly from the circular portion, as shown in FIG. 15B. The base 1515 of the button attachment 1510 is placed through the circular portion 1550 of the hole and the post 1520 is slid along the slot portion 1555 such that the central post 1520 extends through the slot 1555 with the base 1515 being too large to fit through the slot thereby "locking" the button within the slot. The nut 1525 is then engaged with the post 1520 such that the occipital attachment 105 is secured to the button 1510 using the coupler 1530, as shown in FIG. 16. In this way, the head 1515 of the button attachment 1510 lies beneath the inner table of the skull and acts as a clamp around the full thickness of the sub-occipital bone.

Figure 17B:
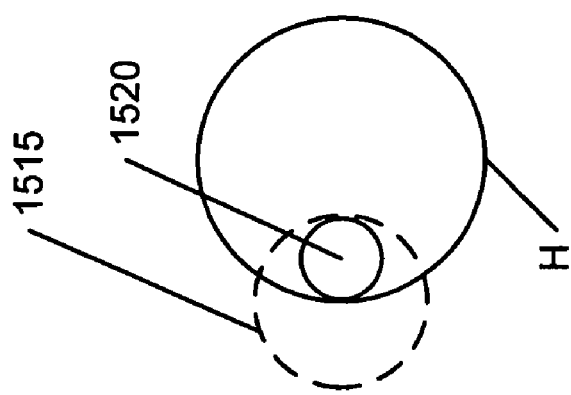
FIG. 17B shows a plan view of an offset button attachment anchored to a bone structure via a hole formed in the bone structure.
Figure 17A:
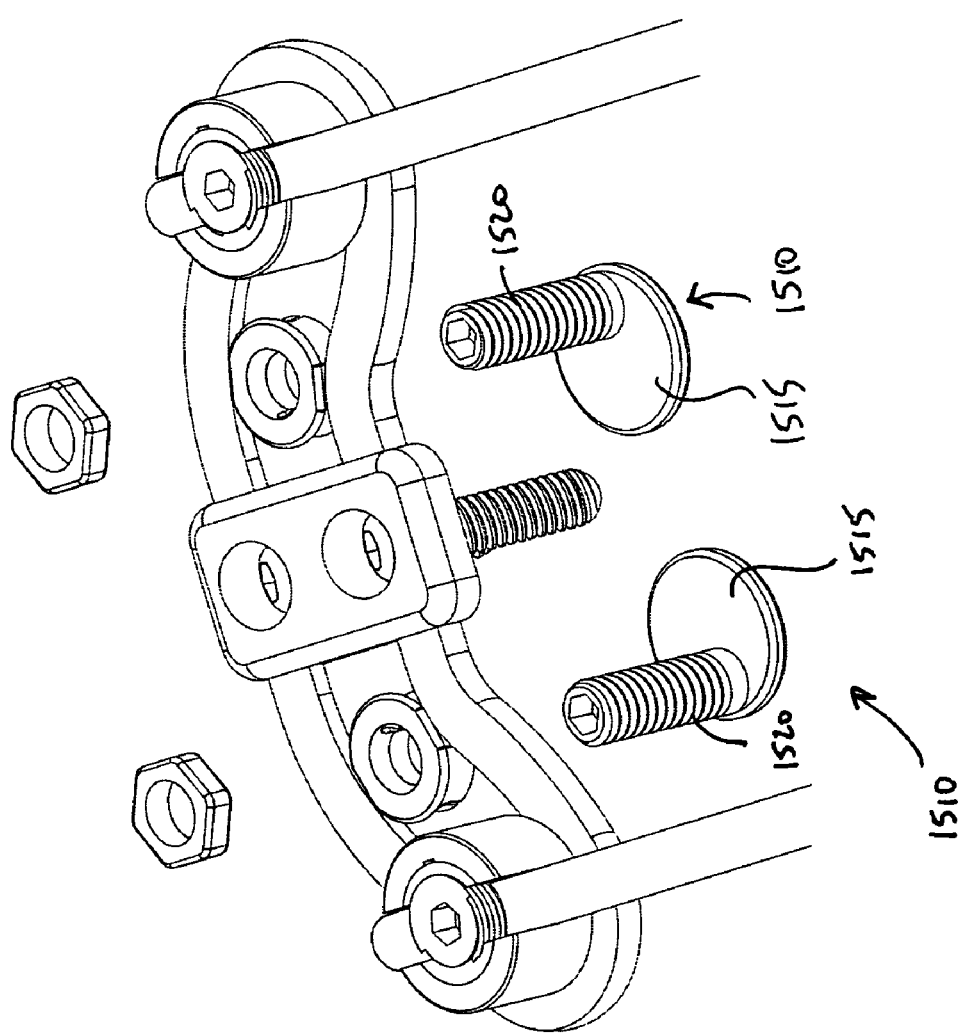
FIG. 17A shows another embodiment of the button attachments.

FIG. 17A shows another embodiment of the button attachments 1510 wherein the posts 1520 are positioned off-center of the base 1515. That is, the posts 1520 are attached to the base 1515 at a location that is distanced from the center point of the base 1515. In the illustrated embodiment, the post 1520 is located at the periphery of the base 1515 at a maximum distance from the centerpoint of the base 1515. However, it should be appreciated that the posts 1520 can be positioned at a variety of locations off-center of the base.

Figure 17C:
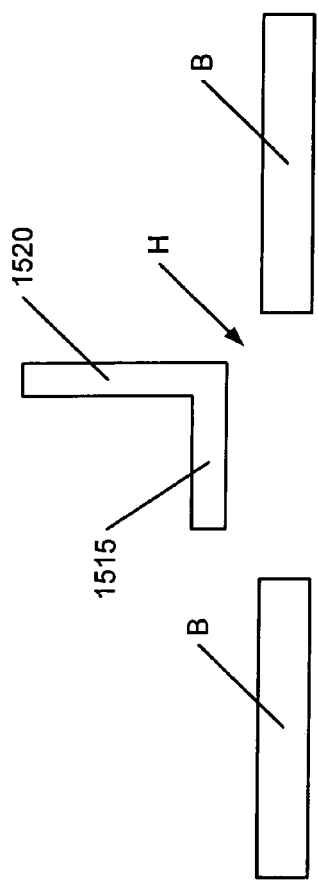
FIG. 17C shows a cross-sectional side view of the button attachment positioned above the hole in the bone structure prior to insertion.
Figure 17D:
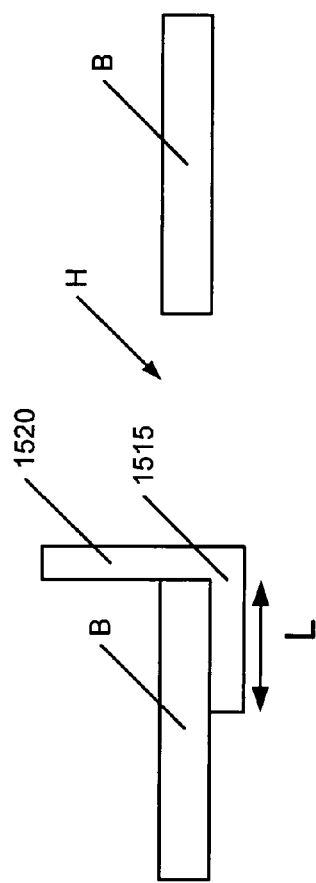
FIG. 17D shows a cross-sectional side view of the button attachment after insertion through the hole and anchored to the bone structure.

The use of the button attachments 1510 with the off-center post is now described with reference to FIGS. 17B-17D. FIG. 17B shows a plan view of the button attachment 1510 anchored to a bone structure B via a hole H formed in the bone structure B. For clarity of illustration, the base 1515 is shown in phantom lines. FIG. 17C shows a cross-sectional side view of the button attachment 1510 positioned above the hole H in the bone structure B prior to insertion. FIG. 17D shows a cross-sectional side view of the button attachment 1510 after insertion through the hole H and anchored to the bone structure B.

With reference to FIG. 17C, the button attachment 1510 is first positioned above the hole H that was previously formed in the bone structure B. Note that the hole H is not required to have a keyhole shape, although a keyhole shape can be used if desired. The base 1515 of the button attachment 1510 is then moved into or through the hole H and is slid laterally until the post 1520 abuts the bony edge of the hole, as shown in FIG. 17D. Thus, the base of the button attachment 1510 is inserted through the hole and moved laterally such that a side of the post 1520 abuts the bony edge of the hole.

As best shown in FIG. 17D, an upper surface of the base 1515 contacts an underside of the bone structure B in a manner that provides sufficient contact therebetween such that the base 1515 anchors in a hook-like manner to the bone structure B. The base 1515 desirably has a transverse dimension that is less than the transverse dimension of the hole H to permit the base to be inserted through the hole. Moreover, the base desirably has a transverse offset length L (shown in FIG. 17D) that is offset from the post 1520 wherein the transverse offset length L provides the base 1515 with a size or contact area sufficient to anchor to the bone structure. It should be appreciated that the base 1515 can have a wide variety of shapes that permit the base 1515 to anchor to the underside of the bone structure.

Multi-Axial Connectors

There is now described a multi-axial occipito-cervical connection system that enables the occipital rod 115 to be coupled to the cervical rod 120 in a manner that permits multi-axial, relative movement between the two rods about a predetermined location, such as the heads of the rods. The system includes a locking mechanism that can be actuated to lock the relative positions of the rods. As mentioned, the rods can provide an interconnection between an attachment(s) on the skull (such as the occipital attachment) and an attachment(s) to the spine (such as spine screw(s)). It should be appreciated that various other interconnecting members can be used in place of the rods, some of which are described below.

Figure 18:
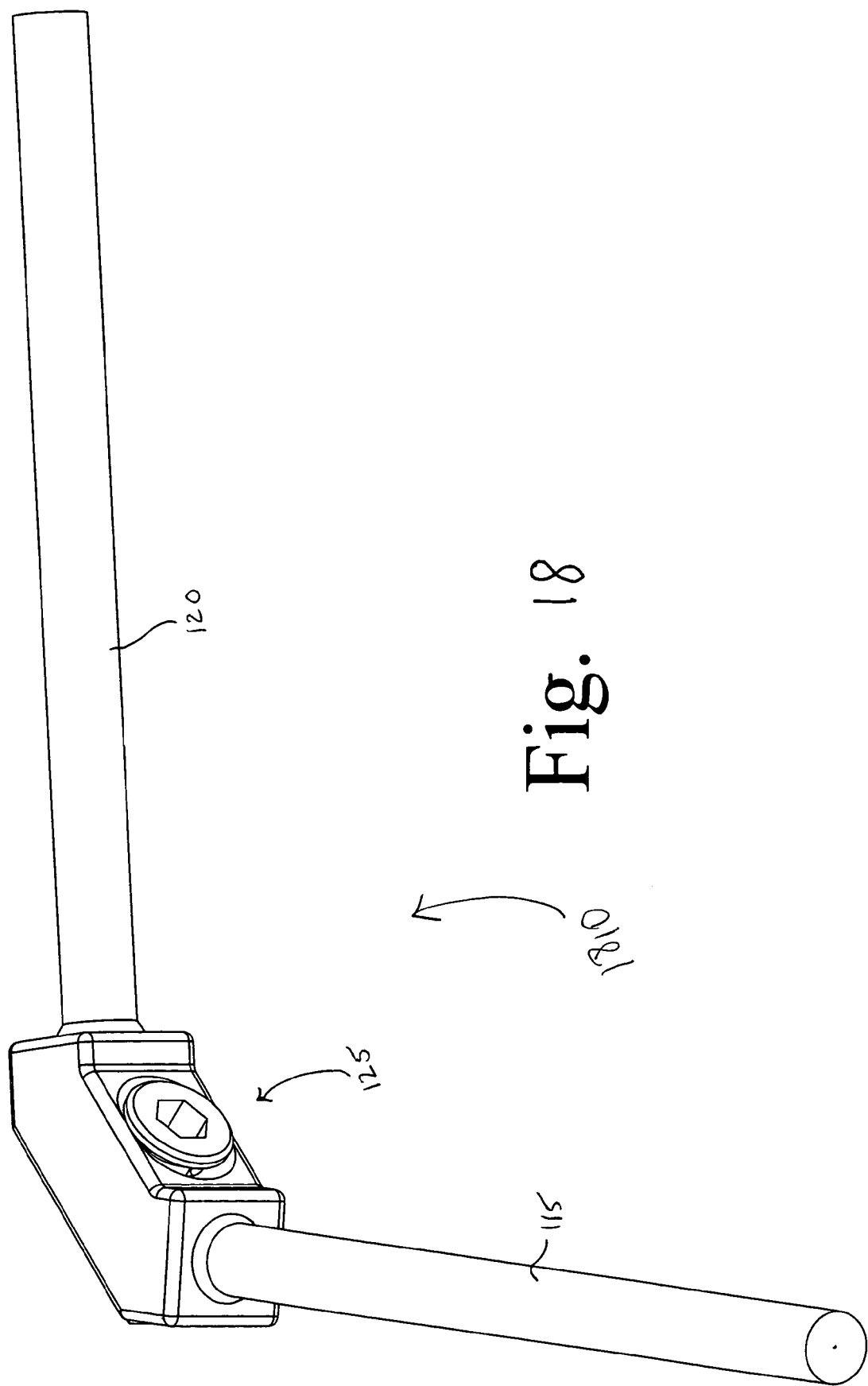
FIG. 18 shows a perspective view of a first embodiment of a multi-axial occipito-cervical connection system.

FIG. 18 shows a perspective view of a first embodiment of a multi-axial occipito-cervical connection system 1810 that includes the multi-axial connector 125, the occipital rod 115, and the cervical rod 120. The multi-axial connector 125 permits the distal ends of the occipital rod 115 and the cervical rod 120 to mate with respective occipital and cervical attachments without having to contour the rods, as described in detail below. Advantageously, the multi-axial connector 125 connects the occipital rod 115 to the cervical rod 120 in such a way that the two rods can be adjusted over multiples axes relative to each other.

Figure 19:
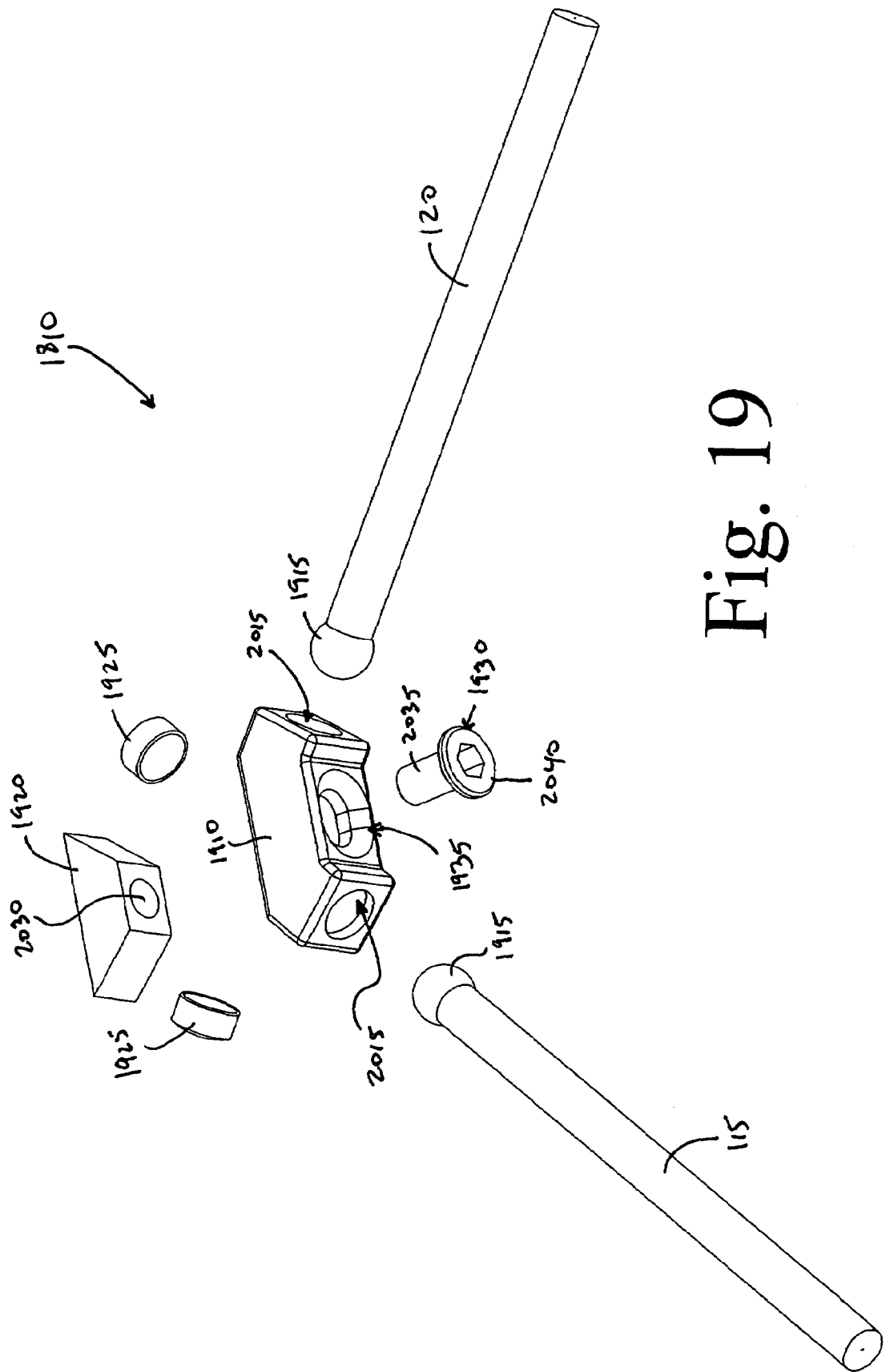
FIG. 19 shows a perspective, exploded view of the first embodiment of the multi-axial occipito-cervical connection system.

FIG. 19 shows an exploded view of the multi-axial connector 125, which includes a main housing 1910 that couples to a head 1915 located on a proximal end of each of the rods 115 and 120. The multi-axial connector 125 further includes a locking member 1920 that can be positioned at least partially within the housing 1910. The locking member 1920 preferably interacts with a pair of caps 1925 that each interact with a respective head 1915 of the rods 115,120 to lock the position of the rods relative to one another, as described below. An actuator member 1930 adjustably engages the housing 1910 (via a channel 1935 in the housing 1910) and the locking member 1920 (via a bore 2030 in the locking member 1920) to control locking of the orientation of the rods 115, 120, as described in more detail below.

Figure 20:
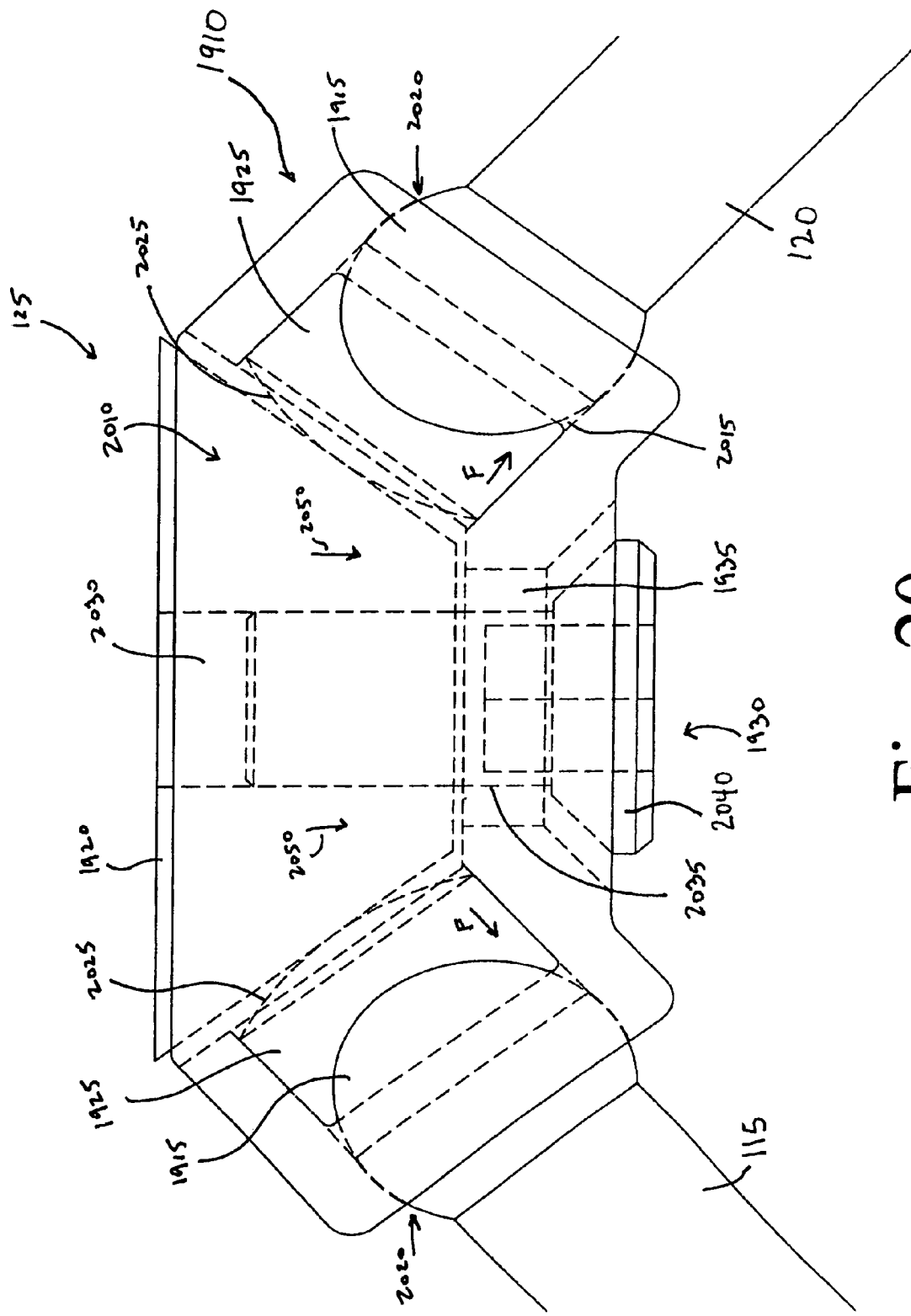
FIG. 20 shows a cross-sectional view of the multi-axial connector in an assembled state and coupled to the occipital rod and the cervical rod.

FIG. 20 shows a cross-sectional view of the multi-axial connector 125 in an assembled state and coupled to the occipital rod 115 and the cervical rod 120. In the illustrated embodiment, the housing 1910 has a central portion with an internal, wedge-shaped cavity 2010 that receives the locking member 1920. The locking member 1920 has a complementary wedge-shape that fits within the cavity 2010. Lateral portions of the housing 1910 each include a bore 2015 that forms an opening 2020 in the housing 1910.

The spherical head 1915 of each rod is sized to fit within a corresponding bore 2015. The opening 2020 for each bore 2015 is smaller than the maximum transverse dimension of the corresponding head 1915 but greater than the transverse dimension of the rod attached to the head 1915. Thus, the head 1915 cannot slide through the opening 2020 although the rod is small enough to slide through the opening 2020. When the head 1915 of a rod is positioned within a corresponding bore 2015 as shown in FIG. 19, the smaller opening prevents the head 1915 from sliding out of the housing 1910 through the opening 2020.

With reference still to FIG. 20, a cap 1925 sits atop the head 1915 of each rod. Each cap 1925 has an abutment surface 2025 that extends at least partially into the cavity 2010. The locking element 1920 sits within the cavity 2010 such that a locking caps 1925 is interposed between the locking element 1920 and a respective head 1915 of a rod. Alternately, the cap(s0 1925 may be eliminated altogether and the side arms of the housing 1910 made sufficiently shallow so that a portion of the heads 1915 sits within the cavity 2010. In this way, the locking element makes direct contact with the heads 1915. The locking element 1920 includes an internally-threaded mid-line bore 2030 that aligns with the channel 1935 of the housing 1910 when the locking element 1920 is positioned within the cavity 2010. In an alternative embodiment, the caps 1925 are not present and the heads 1915 directly contact the locking element 1920. This allows the size of the housing 1910.

In the embodiment shown in FIG. 20, the actuator member 1930 comprises a screw having a threaded post 2035 and a screw head 2040. The threaded post 2035 is sized and shaped to engage the threaded bore 2030 in the locking element 1920. The head 2040 of the actuator member 1930 can include a coupling structure, such as, for example, a hexagonal cavity, that is configured to receive a complimentary driver, such as, for example, an Allen-style wrench, for rotating and driving the actuator member 1930 into the locking element 1920.

The mechanism for adjusting and locking the rods using the multi-axial connector 125 is now described. After the distal end of each rod is fixed to either the occipital or cervical attachment(s), the actuator 1930 comprised of the screw is tightened into the locking element 1920. The tightening of the actuator 1930 draws the locking element 1920 deeper into the wedge-shaped cavity 2010 in the housing 1910, as exhibited by the arrows 2050 in FIG. 20. As the locking element 1920 advances deeper into the cavity 2010, it contacts the curvilinear abutment surface 2025 of each cap 1925 and drives the caps 1925 further into the bores 2015. The caps 1925 exert a force F on the heads 1915 of the rods. The force F causes the spherical heads 1915 to sit tightly within the respective bores 2015 and immobilizes the spherical head 1915 of each rod within the respective bore in the housing 1920. In this way, the position of the rods 115 and 120 and/or bore 2015 are locked. The heads of the rods and the abutment surface 2025 of the caps 1925 may be further textured or ridged in order to increase the frictional contact between them and thereby increase the holding power of the device.

Figure 21:
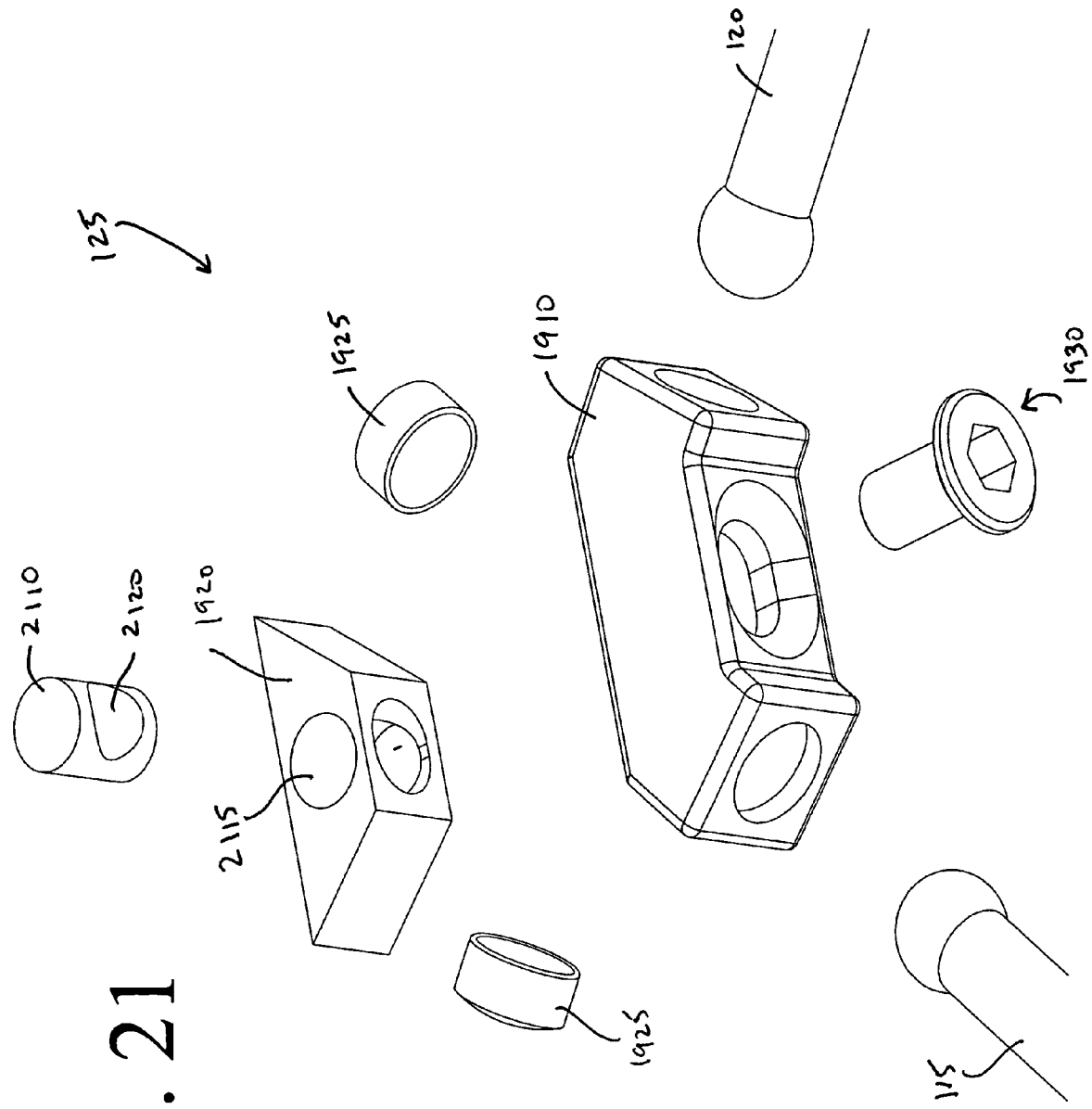
FIGS. 21-25 show additional embodiments of the multi-axial connector.

FIG. 21 shows another embodiment of the multi-axial connector 125 in which a barrel nut 2110 is positioned inside a bore 2115 the locking member 1920. The barrel nut 2110 has a threaded bore 2120 that is sized to receive a complementary-threaded post 2035 of the actuator member 1930 for tightening the locking member 1920 within the housing 1910.

Figure 22:
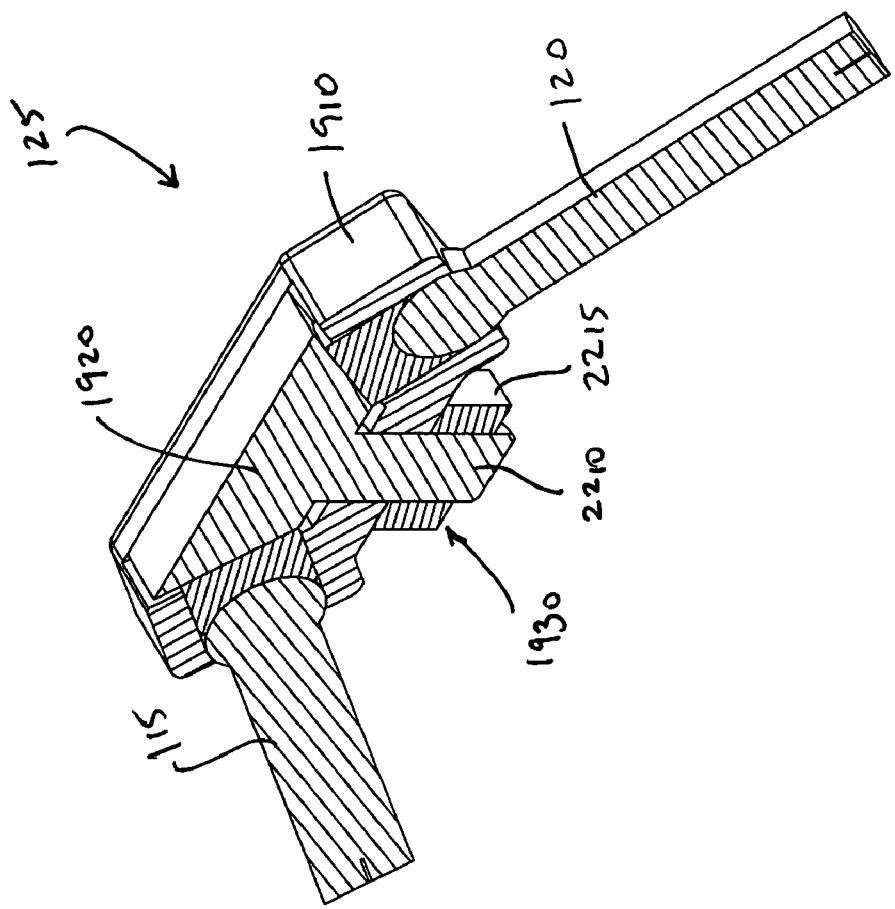

It should be appreciated that various other mechanisms can be used to lock the position of the rods. For example, FIG. 22 shows an embodiment of the multi-axial connector 125 wherein the locking member 1920 has a threaded post 2210 that protrudes out of the housing 1910. The actuator member 1930 comprises a threaded nut 2215 that engages the post 2210. The nut 2215 is tightened to pull the locking member 1920 deeper into the cavity of the housing 1910 and lock the position of the rods 115,120.

Figure 23:
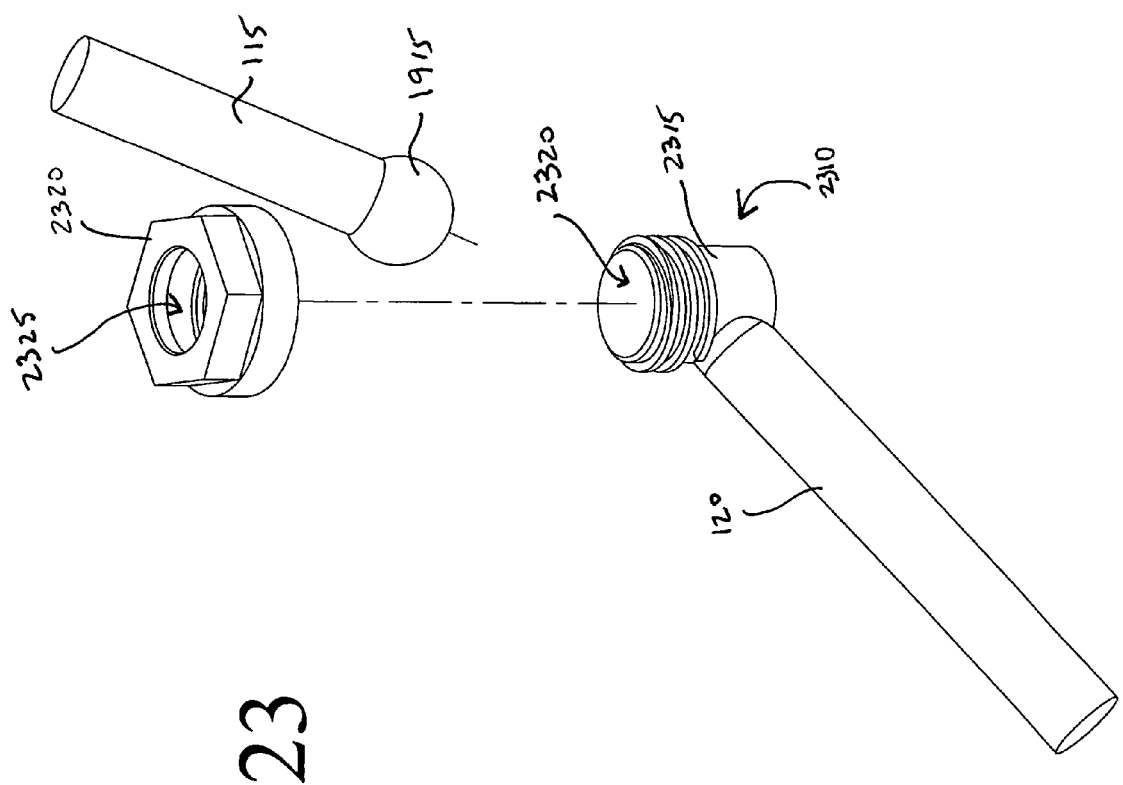

FIG. 23 shows yet another embodiment of the multi-axial connector, wherein the multi-axial connector 2310 is integrated into the distal end of one of the rods. The multi-axial connector 2310 is shown integrated into the rod 120, although it should be appreciated that it can be integrated into either rod 115 or 120. In this embodiment, the multi-axial connector 2310 comprises a cup member 2315 having an internal cavity 2320 sized to receive the head 1915 of the rod 115. A locking member comprised of a threaded nut 2320 has a bore hole 2325 that is sized to receive the rod 115 but smaller than the head 1915 of the rod 115. The head 1915 can be secured in the cup 2315 and tightened therein by tightening the nut 2320 with the rod in a desired orientation.

Figure 24:
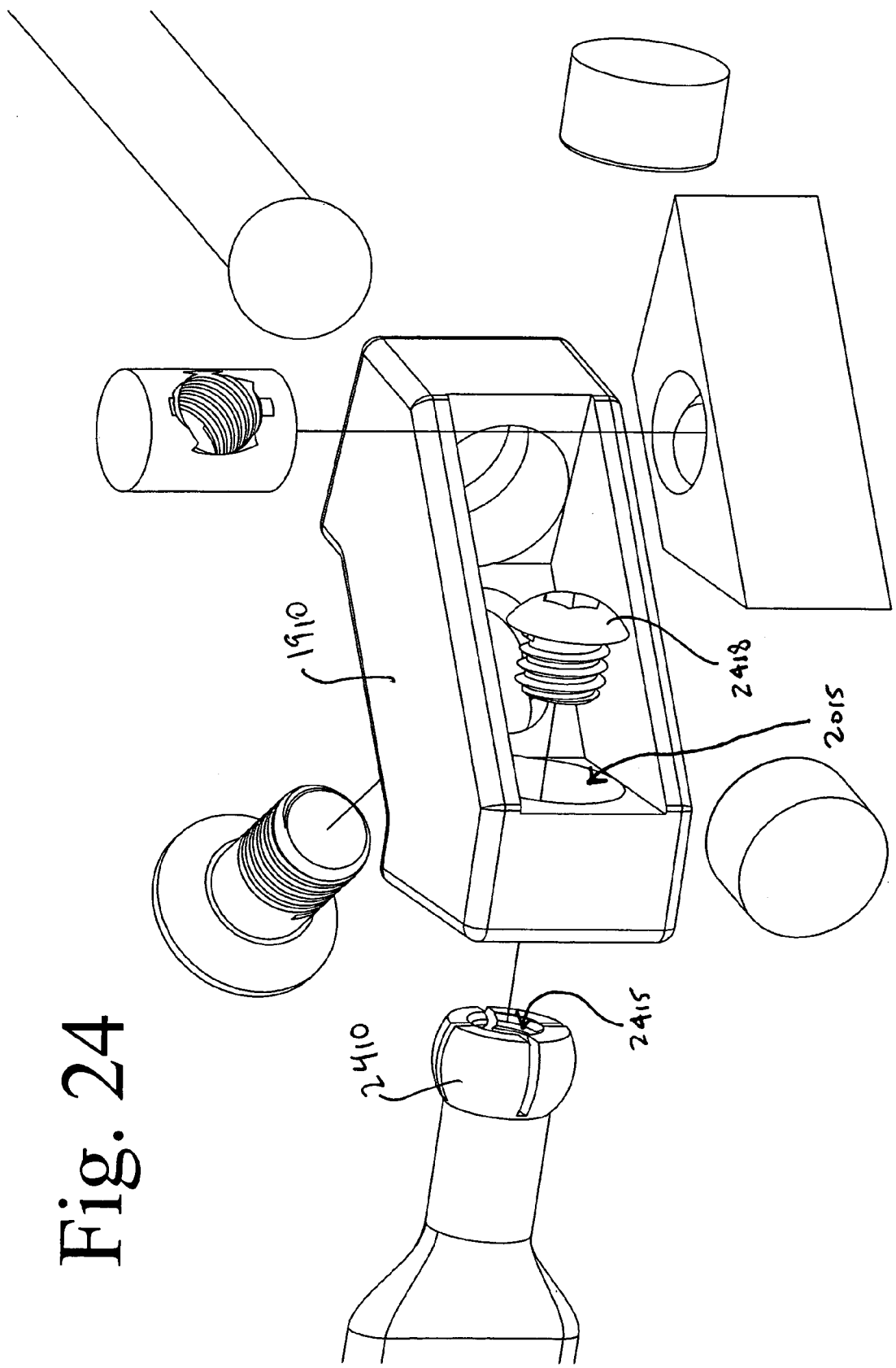
Figure 25:
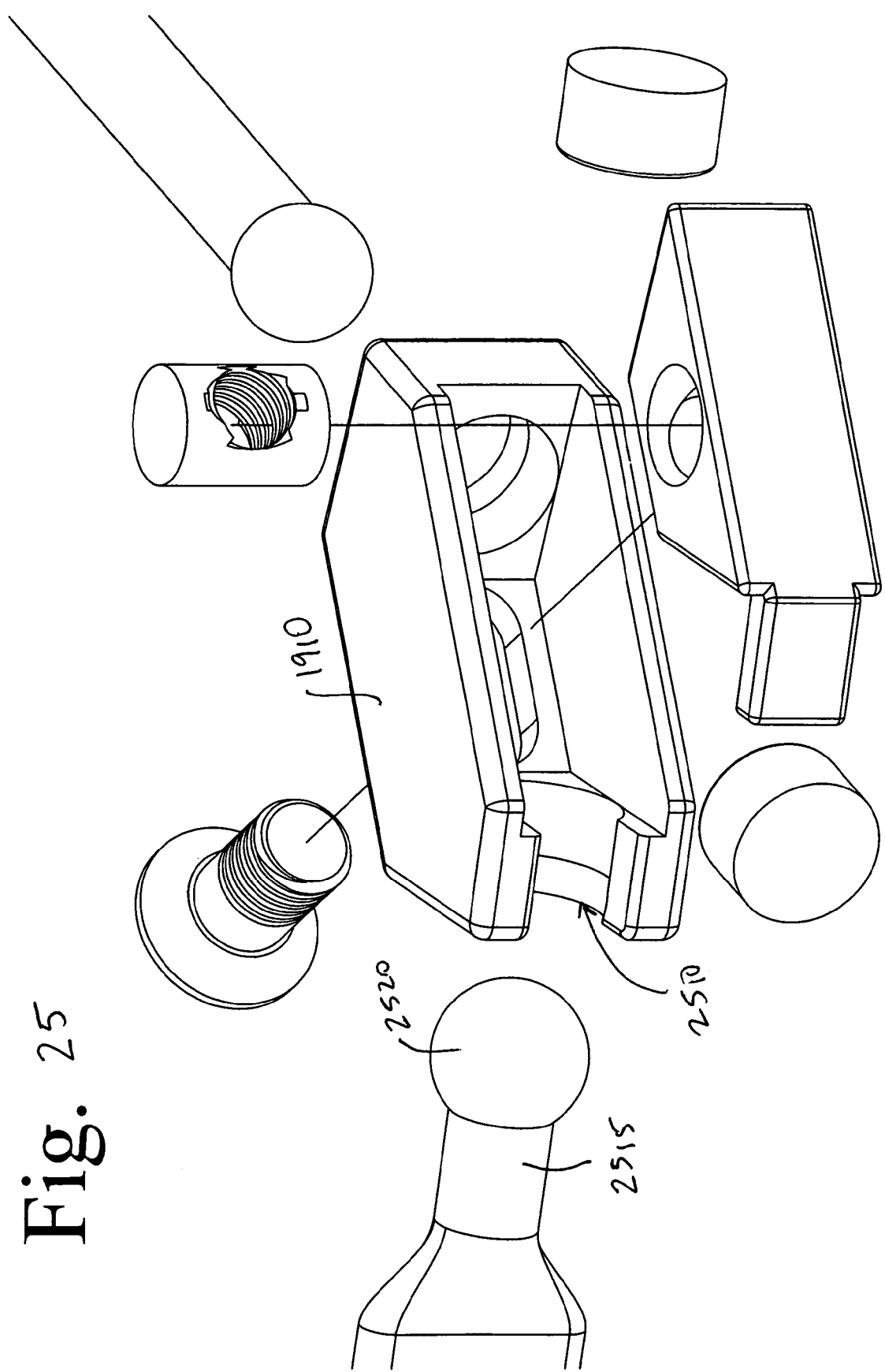

FIG. 24 shows yet another embodiment of the multi-axial connector wherein at least one of the rods utilizes a collapsible head 2410. The head 2410 has a threaded bore 2415 that receives a screw 2418. The collapsible head 2410 can be pushed into the bore 2015 in the housing 1910. Once inside the bore 2015, the threaded screw 2418 mates with and expands the head 2410 rendering the head un-collapsible such that the head 2410 is retained in the housing 1910. Alternatively, one side of the bore may be cut away as illustrated in FIG. 25. The diameter of the cut opening 2510 is greater than that of a neck 2515 but less than that of the head 2520 of the rod, permitting the placement and retention of the head 2520 within the bore in the housing 1910.

Method of Use

In use, the occipital attachment 105 is placed at the posterior aspect of the skull and centered over the midline of the underlying bone. The device is preferably, but not necessarily anchored into the sub-occipital skull.

The occipital attachment 105 attaches to the occipital bone or sub-occipital bone of the skull using the bone screws 130 (shown in FIG. 1), which are placed through the bore holes 312 within central body 305 and into the midline of the underlying bone. The bone screws 130 follow the angled trajectory of the bore holes 312 and attach to the underlying bone in a trajectory that is not perpendicular to the bone surface. As mentioned, additional bone screws, button attachments or other fasteners (cables, etc) may be placed into the central body 305 through the apertures 315 to provide additional fixation. The screws can be placed in a cross-screw configuration to enhance the attachment of the occipital attachment with the skull.

Each rod is cut to appropriate length. On each side of the occipital attachment 105, an occipital rod 115 is attached to the occipital attachment 105 via the rod fixation assembly 110 (shown in FIG. 1). The cervical rods 120 are then attached to at least a portion of the cervical spine 2115 using one or more cervical attachments in a well-known manner. The cervical rod 120 is preferably locked into the cervical attachment(s) first. Subsequently, the occipital rod 115 is locked into the rod fixation assembly 110 of the occipital attachment 105.

The multi-axial connector 125 couples the occipital rod 115 to the cervical rod 120. After the rods have been attached as described above, the multi-axial connector between the two rods is then locked. While the preferred order of lock deployment is illustrated, the locks may be deployed in any order that the surgeon prefers. Once all connection points are tight, the construct is rigid. Advantageously, the multi-axial connector 125 permits multi-axial movement of the rods 115, 120 relative to one another about the center of the respective heads that are attached to the multi-axial connector over a defined distance. The relative positions and orientations of the rods can be adjusted and then locked in the desired orientation and position. Advantageously, this does away with the need in prior art devices to contour the inter-connecting rod between the skull and the spine.

Additional Embodiments

Figure 26:
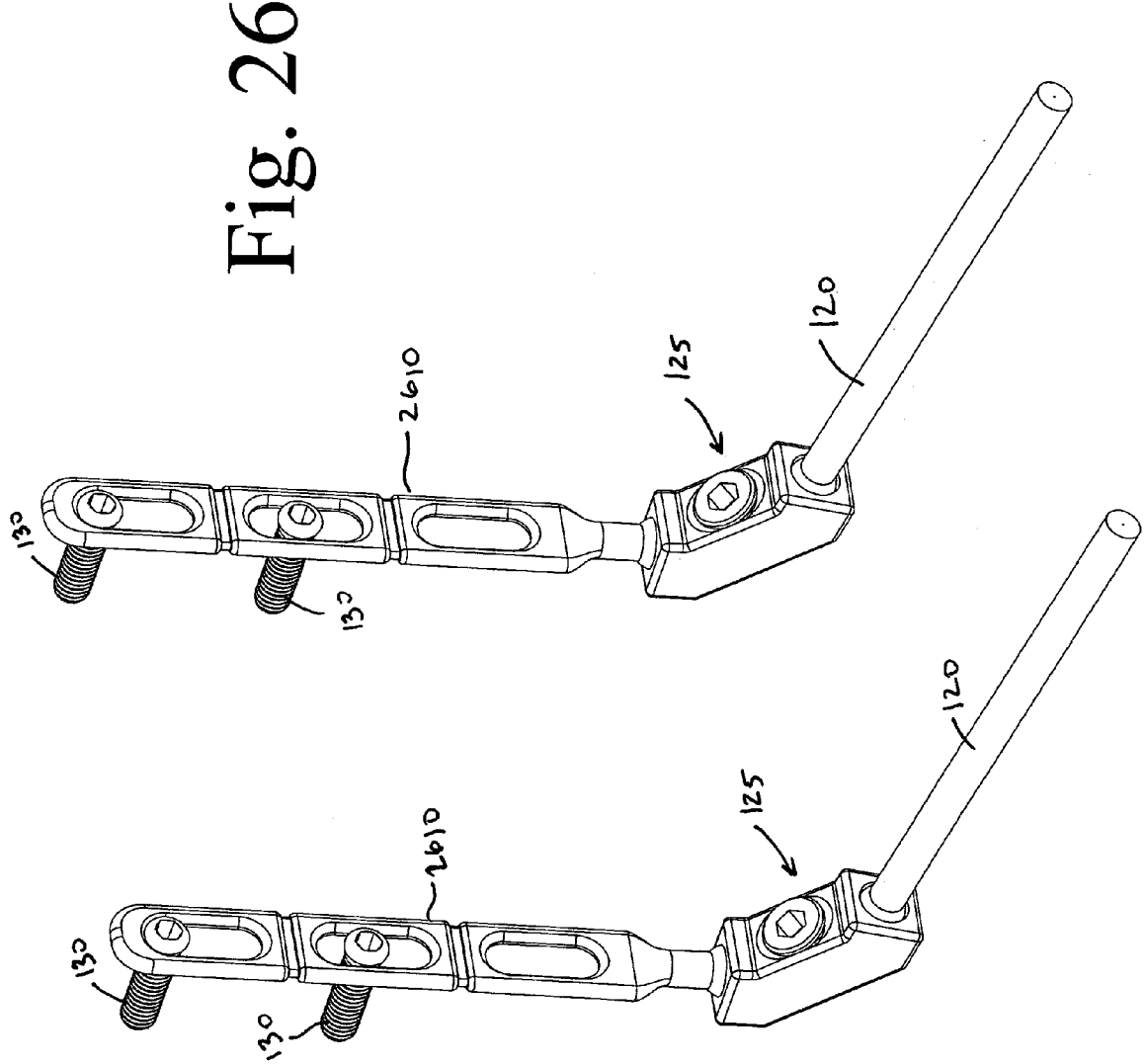
FIGS. 26-27 show other embodiments wherein the occipital rods are replaced with elongated plate members.

FIG. 26 shows another embodiment wherein the occipital rods 115 are replaced with elongated plate members 2610 and attached to the cervical rods 120 via any embodiments of the multi-axial connectors 125. The plate members 2610 are elongated and include one or more apertures that are sized to receive attachment devices, such as screws 130, for attaching the plate members 2610 to the skull. Other types of attachment devices, such as buttons, can be used to attach the plate members 2610 to the skull. The embodiment shown in FIG. 26 eliminate the need for the occipital attachment 105 shown in FIG. 1 as the plate members 2610 attach directly to the skull.

Figure 27:
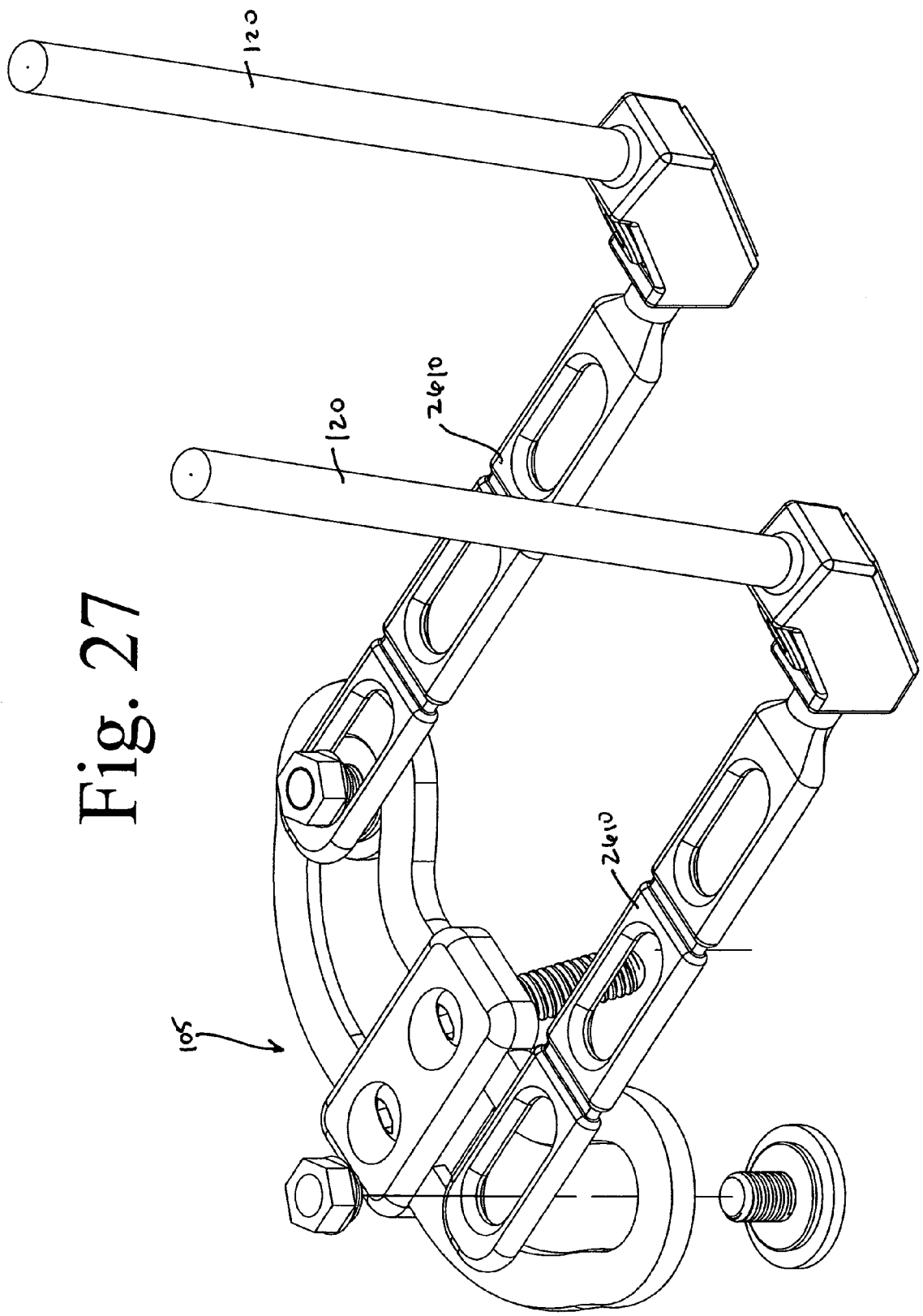

FIG. 27 shows another embodiment wherein the occipital attachment 105 is used in combination with the plate members 2610 and with the cervical rods 120. it should be appreciated that in any of the embodiments, the cervical rods 120 can also be replaced with plate members that are attached to a portion of the spine.

Figure 28:
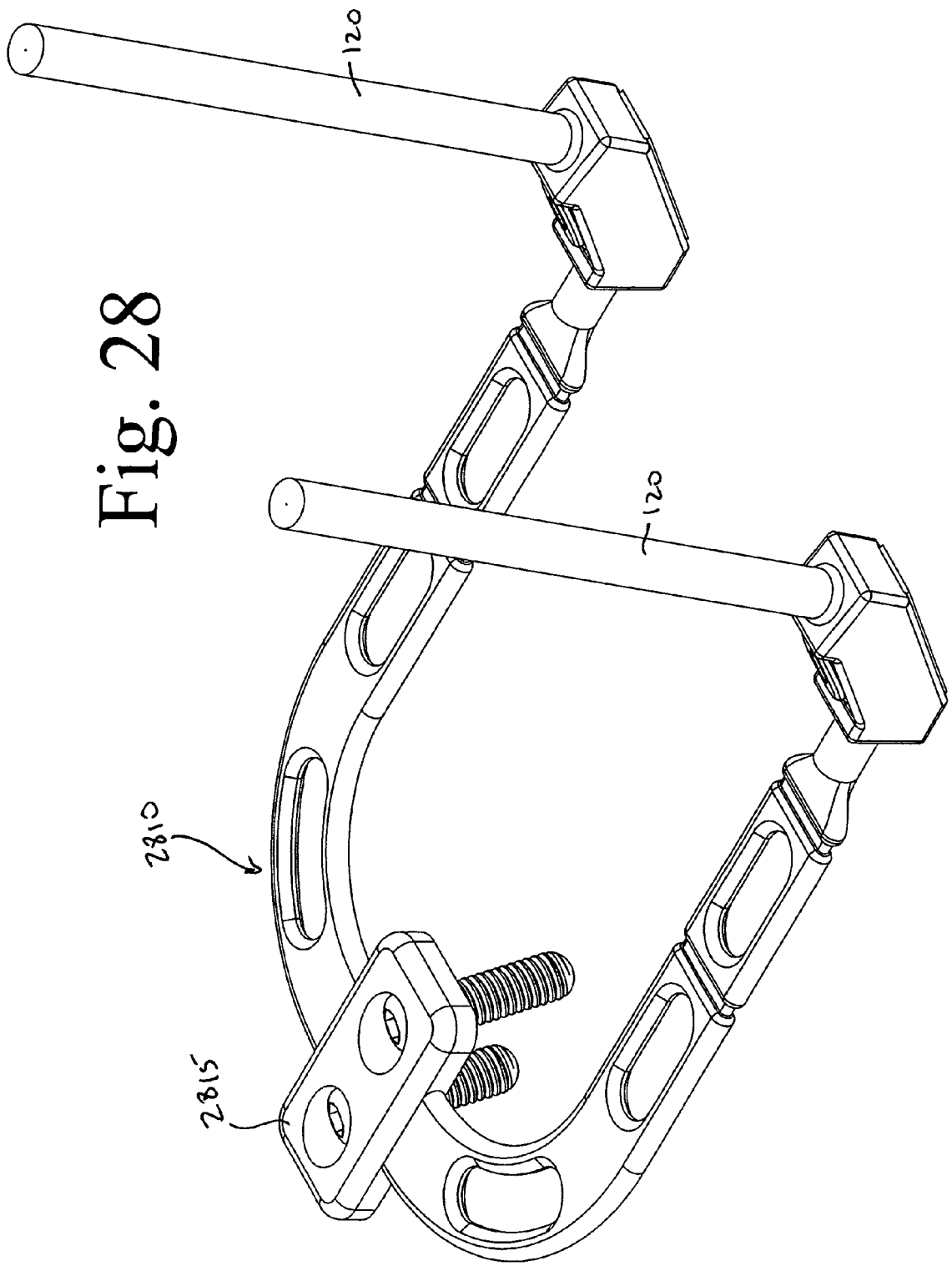
FIG. 28 shows yet another embodiment wherein the occipital rods and the occipital attachment are collectively replaced by a u-shaped plate.

FIG. 28 shows yet another embodiment wherein the occipital rods 115 and the occipital attachment 105 are collectively replaced by a skull connector comprising a "U"-shaped plate 2810 having a central member 2815 that is similar to the central member 305 of the occipital attachment 105. The central member 2815 can differ in thickness from the u-shaped plate 2810 or it can be of similar or same thickness. The central member 2815 has boreholes for receiving bone screws, wherein the boreholes can be perpendicular or non-perpendicular (or a combination thereof) relative to a horizontal, as described above. The "U"-shaped plate 2810 has a plurality of apertures that can receive additional attachment members, such as screws or buttons, for providing additional points for plate fixation to underlying bone. In any of the embodiments described herein, other attachment members, such as cables, etc, can also be used.

A number of embodiments have been described. Nevertheless, it will be understood that various modifications may be made without departing from the spirit and scope of the claims. Accordingly, other embodiments are within the scope of the following claims.

What is claimed is:

1. A bone attachment device, comprising:
a bone attachment member configured to be attached to a bone, the bone attachment member comprising:
 a central plate body member having a top surfaces, bottom surface and multiple side surfaces, the bottom surface being adapted to abut the bone, the body having at least one borehole extending from the top surface to the bottom surface, wherein the borehole is adapted to receive at least one bone fastener;
 at least one extension extending outwardly from the central body, wherein the extension defines a periphery of an internal aperture sized to receive at least one rod fixation assembly;
 a rod fixation assembly in the internal aperture that attaches a first end of an interconnecting fastener to the bone attachment member, wherein a second end of the interconnecting fastener attaches onto a spinal bone; and
 wherein the rod fixation assembly comprises:
  an outer saddle member with a cylindrical outer wall having a top surface, a bottom surface that contacts an upper surface of the bone attachment member, and an internal aperture extending from the top to bottom surfaces along the long axis of the outer saddle member, wherein the aperture concentrically contains an inner saddle member, the outer saddle member further containing a slot adapted to receive the interconnecting fastener, wherein the slot extents from one side to an opposite side of the cylindrical outer wall and wherein the slot extends from the top surface towards the bottom surface for a distance that is greater than the diameter of the interconnecting fastener but less than the total distance from the top to bottom surface; and
  an inner saddle member having a bottom ledge that engages a lower region of the bone attachment member and a cylindrical extension that extends upwardly through the internal aperture of an extension of the bone attachment member, wherein the cylindrical extension has an outer surface that fits concentrically within the internal aperture of the outer saddle member, an open distal end and a threaded internal aperture with threads that extend to the open distal end; and
  a threaded locking nut that is adapted to fit within the open distal end of the inner saddle member and cooperatively engage the threads of the internal aperture of the inner saddle member.

2. The device of claim 1, wherein the bone attachment member comprises a central body and a pair of extensions that extend outwardly from the central body.

3. The device of claim 1, wherein each red extension is U-shaped.

4. The device of claim 1, wherein each red extension is curvilinear.

5. The device of claim 1, wherein each red extension has a flat top surface, a flat bottom surface, and an outer side surface.

6. The device of claim 5, wherein each red extension has an elongated indentation on an inner surface.

7. The device of claim 1, wherein at least one bore of the central body member defines a bone screw insertion trajectory that is non-perpendicular to the bone surface.

8. The device of claim 1, wherein the internal aperture defined by the extension accepts at least one bone fastener.

9. The device of claim 8, wherein the bone fastener can be positioned in the internal aperture lateral to the rod fixation assembly.

10. The device of claim 8, wherein the internal aperture accepts multiple bone fasteners in addition to the rod fixation assembly.

11. The device of claim 10, wherein advancement of the threaded locking nut reversibly transitions the fixation assembly from a first state wherein the interconnecting fastener is movable relative to the bone attachment member to a second state wherein the interconnecting fastener is rigidly affixed relative to the skull attachment member.

12. A method for the immobilization of a skull relative to a cervical spine segment in a human or animal subject, comprising:
providing a skull attachment device configured to be attached to a skull, the skull attachment device comprising:
 (a) a central plate body member having a top surfaces, bottom surface and multiple side surfaces, the bottom surface being adapted to abut the skull, the body having at least one borehole extending from the top surface to the bottom surface, wherein the borehole is adapted to receive at least one bone fastener;
 (b) at least one extension extending outwardly from the central body, wherein the extension defines a periphery of an internal aperture sized to receive at least one rod fixation assembly;

(c) a rod fixation assembly in the internal aperture that attaches a first end of an interconnecting fastener to the skull attachment device, wherein a second end of the interconnecting fastener attaches onto a spinal bone; and wherein the rod fixation assembly comprises:

(i) an outer saddle member with a cylindrical outer wall having a top surface, a bottom surface that contacts an upper surface of the skull attachment device, and an internal aperture extending from the top to bottom surfaces along the long axis of the outer saddle member, wherein the aperture concentrically contains an inner saddle member, the outer saddle member further containing a slot adapted to receive the interconnecting fastener, wherein the slot extents from one side to an opposite side of the cylindrical outer wall and wherein the slot extends from the top surface towards the bottom surface for a distance that is greater than the diameter of the interconnecting fastener but less than the total distance from the top to bottom surface; and (ii) an inner saddle member having a bottom ledge that engages a lower region of the skull attachment device and a cylindrical extension that extends upwardly through the internal aperture of an extension of the bone attachment device, wherein the cylindrical extension has an outer surface that fits concentrically within the internal aperture of the outer saddle member, an open distal end and a threaded internal aperture with threads that extend to the open distal end; and (iii) a threaded locking nut that is adapted to fit within the open distal end of the inner saddle member and cooperatively engage the threads of the internal aperture of the inner saddle member;

attaching a the skull attachment device rigidly onto the skull using at least one bone screw, wherein the rod fixation assembly is configured to seat a first interconnecting fastener and to reversibly transition from a first state wherein the interconnecting fastener is movable relative to the skull attachment device to a second state wherein the interconnecting fastener is rigidly affixed relative to the skull attachment device;

attaching a spine attachment device onto at least a segment of the cervical spine;

positioning an interconnecting device between the skull attachment device and the spine attachment device, wherein the interconnecting device contains at least a first interconnecting fastener, a second interconnecting fastener, and an interconnecting fastener connector which is adapted to reversibly transition from a first state wherein the first and second interconnecting fasteners are movable relative to one another to a second state wherein the first and second interconnecting fasteners are rigidly affixed to each other;

attaching the first interconnecting fastener to the skull attachment device and the second interconnecting fastener to the cervical spine attachment device;

rigidly immobilizing the first interconnecting fastener relative to the skull attachment device and the second interconnecting fastener relative to the spine attachment device, wherein the interconnecting fastener connector remains in the first, non immobilized, state;

transitioning the interconnecting fastener connector into the second, rigid state so as to rigidly immobilize the attached segment of the skull relative to the attached segment of the cervical spine.

13. The method of claim 12, wherein the skull and the cervical spine are positioned into a desired spatial relationship before transitioning the interconnecting fastener connector into the second, rigid state.

* * * * *

UNITED STATES PATENT AND TRADEMARK OFFICE
CERTIFICATE OF CORRECTION

PATENT NO. : 7,618,443 B2
APPLICATION NO. : 11/153258
DATED : November 17, 2009
INVENTOR(S) : M. Samy Abdou It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 972 days.

Signed and Sealed this

Twenty-sixth Day of October, 2010

David J. Kappos
*Director of the United States Patent and Trademark Office*